(12) United States Patent
Brahmbhatt et al.

(10) Patent No.: US 8,772,013 B2
(45) Date of Patent: *Jul. 8, 2014

(54) METHODS FOR TARGETED IN VITRO AND IN VIVO DRUG DELIVERY TO MAMMALIAN CELLS VIA BACTERIALLY DERIVED INTACT MINICELLS

(75) Inventors: Himanshu Brahmbhatt, Sydney (AU); Jennifer MacDiarmid, Sydney (AU)

(73) Assignee: Engeneic Molecular Delivery Pty Ltd, Sydney (AU)

( * ) Notice: Subject to any disclaimer, the term of this patent is extended or adjusted under 35 U.S.C. 154(b) by 469 days.

This patent is subject to a terminal disclaimer.

(21) Appl. No.: 10/588,028

(22) PCT Filed: Jan. 27, 2005

(86) PCT No.: PCT/IB2005/000204

§ 371 (c)(1), (2), (4) Date: Apr. 30, 2007

(87) PCT Pub. No.: WO2005/079854

PCT Pub. Date: Sep. 1, 2005

(65) Prior Publication Data

US 2008/0051469 A1 Feb. 28, 2008

Related U.S. Application Data

(60) Provisional application No. 60/540,590, filed on Feb. 2, 2004.

(51) Int. Cl.
*C12N 1/20* (2006.01)
*A61K 47/00* (2006.01)
*A61K 47/46* (2006.01)
*A61K 31/337* (2006.01)

(52) U.S. Cl.
USPC ............ 435/252.1; 435/252.8; 514/772; 514/773; 514/325

(58) Field of Classification Search
USPC ............ 435/252.1, 252.8; 514/773, 777, 772, 514/325
See application file for complete search history.

(56) References Cited

U.S. PATENT DOCUMENTS

| | | | |
|---|---|---|---|
| 5,316,771 A | 5/1994 | Barenholz et al. | |
| 6,635,448 B2 | 10/2003 | Bucciarelli et al. | |
| 7,011,946 B2 | 3/2006 | RayChaudhuri et al. | |
| 7,125,679 B2 | 10/2006 | Ashkar | |
| 7,183,105 B2 * | 2/2007 | Sabbadini et al. | 435/320.1 |
| 2003/0166099 A1 | 9/2003 | Sabbadini et al. | |
| 2003/0199088 A1 | 10/2003 | Sabbadini et al. | |
| 2003/0203481 A1 | 10/2003 | Surber et al. | |
| 2004/0265994 A1 | 12/2004 | Brahmbhatt et al. | |
| 2007/0237744 A1 | 10/2007 | Brahmbhatt et al. | |
| 2007/0241067 A1 | 10/2007 | Brahmbhatt et al. | |
| 2007/0298056 A1 | 12/2007 | Brahmbhatt et al. | |
| 2008/0038296 A1 | 2/2008 | Brahmbhatt et al. | |
| 2008/0299084 A1 | 12/2008 | Brahmbhatt et al. | |

FOREIGN PATENT DOCUMENTS

| | | |
|---|---|---|
| WO | WO 86/01102 | 2/1986 |
| WO | WO 96/26715 | 9/1996 |
| WO | WO 96/32930 | 12/1996 |
| WO | WO 98/18450 | 5/1998 |
| WO | WO-00/63364 A2 | 10/2000 |
| WO | WO 02/072759 A2 | 9/2002 |
| WO | WO 03/033519 A2 | 4/2003 |
| WO | WO 03/072014 A2 | 9/2003 |
| WO | WO-2005/056749 A2 | 6/2005 |
| WO | WO-2006/066048 A2 | 6/2006 |

OTHER PUBLICATIONS

Coldwell et al The Journal of Immunology, 1984, 133, 2 950-957.*
Khatchatourians et al Preparative Biochemistry, 3(3) 1973, 291-298.*
Christen et al Gene, 1983, 23, 195-198.*
Nikaido et al Microbiol. Mol. Biol. Rev.2003, 67, 593-656.*
Beveridge et al (Journal of Bacteriology, 1999, 4725-4733.*
Search Report from Singapore App. No. 0705648-4 received Oct. 8, 2008.
Suzuki et al., "Production in *Escherichia coil* of biologically active secretin, a gastrointestinal hormone", Proc. Natl. Acad. Sci. USA 1982, vol. 79, pp. 2475-2479.
Singapore Search Report Application No. 200705647-6.
Alan Bridge et al., "Induction of an interferon response by RNAi vectors in mammalian cells," Nature Genetics, vol. 34, No. 3, (2003), pp. 263-264.
Catherine Grillot-Courvalin et al., "Wild-type intracellular bacteria delivery DNA into mammalian cells," Cellular Microbiology, vol. 4, No. 3, (2002), pp. 177-186.
H. Brahmbhatt et al., U.S. PTO Notice of Allowance, U.S. Appl. No. 10/602,021 dated Jun. 22, 2009, 5 pgs.
H. Brahmbhatt et al., U.S. PTO Office Action, U.S. Appl. No. 10/581,990 dated Mar. 19, 2009, 32 pgs.
H. Brahmbhatt et al., U.S. PTO Office Action, U.S. Appl. No. 10/602,021 dated May 4, 2006, 10 pgs.

(Continued)

*Primary Examiner* — Anoop Singh
(74) *Attorney, Agent, or Firm* — Foley & Lardner LLP

(57) ABSTRACT

A composition comprising intact minicells that contain a drug molecule is useful for targeted drug delivery. One targeted drug delivery method employs bispecific ligands, comprising a first arm that carries specificity for a bacterially derived minicell surface structure and a second arm that carries specificity for a mammalian cell surface receptor, to target drug-loaded minicells to specific mammalian cells and to cause endocytosis of the minicells by the mammalian cells. Another drug delivery method exploits the natural ability of phagocytic mammalian cells to engulf minicells without the use of bispecific ligands.

11 Claims, 6 Drawing Sheets

(56) References Cited

OTHER PUBLICATIONS

H. Brahmbhatt et al., U.S. PTO Office Action, U.S. Appl. No. 10/602,021 dated May 15, 2007, 10 pgs.
H. Brahmbhatt et al., U.S. PTO Office Action, U.S. Appl. No. 10/602,021 dated Jul. 25, 2008, 10 pgs.
H. Brahmbhatt et al., U.S. PTO Office Action, U.S. Appl. No. 11/211,098 dated Feb. 24, 2009, 24 pgs.
H. Brahmbhatt et al., U.S. PTO Office Action, U.S. Appl. No. 11/211,098 dated Apr. 24, 2008, 38 pgs.
H. Brahmbhatt et al., U.S. PTO Office Action, U.S. Appl. No. 11/211,098 dated Aug. 7, 2009, 23 pgs.
H. Brahmbhatt et al., U.S. PTO Office Action, U.S. Appl. No. 11/691,698 dated Dec. 24, 2008, 13 pgs.
H. Brahmbhatt et al., U.S. PTO Office Action, U.S. Appl. No. 11/765,635 dated Oct. 6, 2009, 40 pgs.
H. Brahmbhatt et al., U.S. PTO Office Action, U.S. Appl. No. 12/053,197 dated Aug. 25, 2009, 25 pgs.
Hao Wu et al., "Small Interfering RNA-induced Suppression of MDR1 (P-Glycoprotein) Restores Sensitivity to Multidrug-resistant Cancer Cells," Cancer Research, vol. 63, Apr. 1, 2003, pp. 1515-1519.
Ian Tomlinson et al., "Methods for Generating Multivalent and Bispecific Antibody Fragments," Methods in Enzymology, vol. 326, (2000), pp. 461-479.
Inder M. Verma et al., "Gene Therapy: Twenty-First Century Medicine," Annu. Rev. Biochem., vol. 74, (2005), pp. 711-738.
J. H. Hong et al., "Antisense Bc12 oligonucleotide in cisplatin-resistant bladder cancer cell lines," BJU International, vol. 90, (2002), pp. 113-117.
Jean-Remi Bertrand et al., "Comparison of antisense oligonucleotides and siRNAS in cell culture and in vivo," Biochemical and Biophysical Research Communications, vol. 296, (2002), pp. 1000-1004.
L. R. Kelland, "Of mice and men": values and liabilities of the athymic nude mouse model in anticancer drug development, European Journal of Cancer, vol. 40, (2004), pp. 827-836.
Leoni A. Kunz-Schughart et al., "The Use of 3-D Cultures for High-Throughput Screening: The Multicellular Spheriod Model," Journal of Biomolecular Screening, vol. 9, (2004), pp. 273-285.
Michael J. McCluskie et al., "Route and Method of Delivery of DNA Vaccine Influence Immune Responses in Mice and Non-Human Primates," Molecular Medicine, vol. 5, (1999), pp. 287-300.
Michele Carbone et al., "Multistep and multifactorial carcinogenesis: when does a contributing factor become a carcinogen?," Seminars in Cancer Biology, vol. 14, (2004) pp. 399-405.
Michele De Palma et al., "In Vivo Targeting of Tumor Endothelial Cells by Systemic Delivery of Lentiviral Vectors," Human Gene Therapy, vol. 14, Aug. 10, 2003, pp. 1193-1206.
Robert S. Kerbel, "What is the optimal rodent model for anti-tumor drug testing?," Cancer and Metastasis Reviews, vol. 17, (1999), pp. 301-304.
Stephen L. Eck et al., "Gene-Based Therapy," Chapter 5, Goodman & Gilman's The Pharmacological Basis of Therapeutics, (1996), pp. 77-102.
Yi Lu et al., "Delivery of adenoviral vectors to the prostate for gene therapy," Cancer Gene Therapy, vol. 6, No. 1, (1999), pp. 64-72.
Notice of Reasons for Rejection Japanese Patent Application No. 2006-551944 dted May 10, 2011.
Letter from Knobbe Martens Olson & Bear LLP dated Feb. 26, 2010.
Manisha P. Desai et al., "The Mechanism of Uptake of Biodegradable Microparticles in Caco-2 Cells Is Size Dependent", Pharmaceutical Research, vol. 14, No. 11, 1997, pp. 1568-1573.
Igor Dmitriev et al., "Ectodomain of Coxsackievirus and Adenovirus Receptor Genetically Fused to Epidermal Growth Factor Mediates Adenovirus Targeting to Epidermal Growth Factor Receptor-Positive Cells", Journal of Virology, Aug. 2000, vol. 74, No. 15, pp. 6875-6884.
Christoph Mamot et al., "Epidermal Growth Factor Receptor (EGFR)-targeted Immunoliposomes Mediate Specific and Efficient Drug Delivery to EGFR- and EGFRvIII-overexpressing Tumor Cells", Cancer Research, Jun. 2003, vol. 63, 3154-3161.
William F. Scherer M.D. et al., "The Viral Range in Vitro of a Malignant Human Epithelial Cell (Strain Hela, Gey)—III. Studies with Pseudolymphocytic Choriomeningitus Virus General Discussion", American Journal of Pathology, Jan.-Feb. 31(1): 31-39 (1954).
Masahisa Watarai et al., "Interaction of Ipa Proteins of *Shigella flexneri* with $\alpha_5\beta_1$ Integrin Promotes Entry of the Bacteria into Mammalian Cells", J. Exp. Med. vol. 183, Mar. 1996, pp. 991-999.
Tibor Pal et al., "Plasmid-Associated Adherence of *Shigella flexneri* in a HeLa Cell Model", Infection and Immunity, Aug. 1989, vol. 57, No. 8, pp. 2580-2582.
William F. Scherer et al., "Studies of the Propagation in Vitro of Poliomyelitis Viruses", Journal of Experimental Medicine, vol. 97, No. 5, pp. 695-710 (1953).
Aline Jaffe et al., "Minicell-Forming Mutants of *Escherichia coli*: Production of Minicells and Anucleate Rods", Journal of Bacteriology, vol. 170, No. 7, Jul. 1988, pp. 3094-3101.
Thomas L. Hale et al., "Characterization of Virulence Plasmids and Plasmid-Associated Outer Membrane Proteins in *Shigella flexneri*, *Shigella sonnei*, and *Escherichia coli*", Infection and Immunity, Apr. 1983, vol. 40, No. 1, pp. 340-350.
Gary J. Doherty et al., "Mechanisms and Endocytosis", Annu. Rev. Biochem. Mar. 14, 2009, 78:31.1-31.46.
Pascal Peschard, "Escape from Cbl-mediated downregulatation: A recurrent theme for oncogenic deregulation of receptor tyrosine kinases", Cancer Cell, Jun. 2003, vol. 3, pp. 519-523.
Emmanouil D. Karagiannis et al., "Minicells overcome tumor drug-resistance", Nature Biotechnology, vol. 27, No. 7, Jul. 2009, pp. 620-621.
Jason Gorman et al., "Visulizing one-dimensional diffusion of proteins along DNA", Nature Structural & Molecular Biology, vol. 15, No. 8, Aug. 2008, pp. 768-774.
First Office Action Chinese Patent Application No. 201010599245.2 dated Nov. 1, 2011.
Tanlin Zhan, "Pharmacological Effects of antineoplastic drugs and their clinical applications", pp. 82, Henan Medical University Press, Apr. 30, 1999.
Search and Examination Report Singapore Patent Application No. 201100772-1 dated Feb. 15, 2012.
Cecile-Marie Koppelman et al., "*Escherichia coli* Minicell Membranes Are Enriched in Cardiolipin", Journal of Bacteriology, Oct. 2001, vol. 183, No. 20, pp. 6144-6147.
Jennifer A. MacDiarmid et al., "Bacterially Derived 400 nm Particles for Encapsulation and Cancer Cell Targeting of Chemotherapeutics", Cancer Cell 11, 431-445, May 2007.

* cited by examiner

METHODS FOR TARGETED IN VITRO AND IN VIVO DRUG DELIVERY TO MAMMALIAN CELLS VIA BACTERIALLY DERIVED INTACT MINICELLS

BACKGROUND OF THE INVENTION

The present invention relates to ongoing efforts to achieve controlled drug release and drug targeting to specific tissues, particularly in the area of cancer chemotherapy. More particularly, the invention relates to targeted drug delivery by means of intact bacterial minicells, which are able to deliver drugs intracellularly, within desired target cells in-vivo and in-vitro. Minicells containing chemical or biochemical drugs constitute novel delivery vehicles, capable of being targeted to specific cells. One method of targeting these vehicles employs bispecific molecules that specifically bind to both a minicell surface structure and a target cell surface structure, such as a receptor. The bispecific ligands mediate an interaction between the minicells and target cells, such that the target cells engulf the minicells, which release their drug payload into the cytoplasm of the target cells. Once cytoplasmically released, the drug acts on intracellular targets, such as intracellular organelles, the nucleus, the cytoskeleton, enzymes, and co-factors, to achieve a therapeutic effect. In another method of drug delivery, phagocytosis- or endocytosis-competent target cells engulf drug-loaded minicells without the use of bispecific ligands.

Currently, most drugs used for treating cancer are administered systemically. Although systemic delivery of cytotoxic anticancer drugs plays a crucial role in cancer therapeutics, it also engenders serious problems. For instance, systemic exposure of normal tissues/organs to the administered drug can cause severe toxicity (Sarosy and Reed, 1993). This is exacerbated by the fact that systemically delivered cancer chemotherapy drugs often must be delivered at very high dosages to overcome poor bioavailability of the drugs and the large volume of distribution within a patient. Also, systemic drug administration can be invasive, as it often requires the use of a secured catheter in a major blood vessel. Because systemic drug administration often requires the use of veins, either peripheral or central, it can cause local complications such as phlebitis. Extravasation of a drug also can lead to vesicant/tissue damage at the local site of administration, such as is commonly seen upon administration of vinca alkaloids and anthracyclines.

Because existing systems for targeted drug delivery are seriously deficient, current cancer drug treatment strategies poorly address the problems that attend systemic drug administration. One approach for addressing these problems involves simply modifying administration schedules or infusion regimens, which may be either bolus, intermittent, or continuous. This approach, however, provides very limited benefits.

Some alternative approaches to intravenous injection also exist, each designed to provide regional delivery, i.e., selective delivery to a tumor region. Examples of such alternatives include polymeric implants, intra-peritoneal infusion, intra-pleural infusion, intra-arterial delivery, chemo-embolization, and inhalation of aerosols. In particular, intra-peritoneal administration of chemotherapy has been studied extensively for ovarian carcinoma and other abdominal tumors (Kirmani et al., 1994; Alberts et al., 1996). Unfortunately, each of these delivery methods, including intra-peritoneal administration, has achieved only marginal success at selectively delivering drugs to a tumor site and reducing side effects.

Other attempts to address the problems with systemic delivery of cytotoxic anticancer drugs include the use of alternative drug formulations and delivery systems, including controlled-release biodegradable polymers, polymeric microsphere carriers and liposomes, as well as the co-administration of cytoprotective agents with antineoplastics. Chonn and Cullis, 1995; Kemp et al., 1996; Kumanohoso et al., 1997; Schiller et al., 1996; Sharma et al., 1996; Sipos et al., 1997.

The use of liposomes as drug carriers for chemotherapeutic agents originally was proposed as a means for manipulating drug distribution to improve anti-tumor efficacy and to reduce toxicity (reviewed by Allen, 1997). Through encapsulation of drugs in a macromolecular carrier, such as a liposome, the volume of distribution is significantly reduced and the concentration of drug in a tumor is increased. This causes a decrease in the amounts and types of nonspecific toxicities, and an increase in the amount of drug that can be effectively delivered to a tumor (Papahadjopoulos and Gabizon, 1995; Gabizon and Martin, 1997; Martin, 1998). Liposomes protect drugs from metabolism and inactivation in plasma. Further, due to size limitations in the transport of large molecules or carriers across healthy endothelia, drugs accumulate to a reduced extent in healthy tissues (Mayer et al., 1989; Working et al., 1994).

To prolong their circulation time, liposomes are coated with polyethylene glycol (PEG), a synthetic hydrophilic polymer (Woodle and Lasic, 1992). The PEG headgroup serves as a barrier, sterically inhibiting hydrophobic and electrostatic interactions with a variety of blood components and plasma opsonins at the liposome surface, and thereby retards recognition of liposomes by the reticuloendothelial system. PEG-coated liposomes are termed "sterically stabilized" (SSL) or STEALTH liposomes (Lasic and Martin, 1995). This technology gave rise to a commercial pharmaceutical formulation of pegylated liposomal Doxorubicin, known as Doxil in the U.S. and Caelyx in Europe. A wide array of other drugs also have been encapsulated in liposomes for cancer treatment (Heath et al., 1983; Papahadjopoulos et al., 1991; Allen et al., 1992; Vaage et al., 1993b; Burke and Gao, 1994; Sharma et al., 1995; Jones et al., 1997; Working, 1998).

Liposomal drug carriers, unfortunately, have several drawbacks. For example, in vivo, drugs often leak out of liposomes at a sufficient rate to become bioavailable, causing toxicity to normal tissues. Similarly, liposomes are unstable in vivo, where their breakdown releases drug and causes toxicity to normal tissues. Also, liposomal formulations of highly hydrophilic drugs can have prohibitively low bioavailability at a tumor site, because hydrophilic drugs have extremely low membrane permeability. This limits drug release once liposomal carriers reach a tumor. Highly hydrophobic drugs also tend to associate mainly with the bilayer compartment of liposomes, causing low entrapment stability due to rapid redistribution of a drug to plasma components. Additionally, some drugs, such as 1-β-D-arabinofuranosylcytosine (ara-C) and methotrexate, only enter tumor cells directly, via membrane transporters Plageman et al., 1978; Wiley et al., 1982; Westerhof et al., 1991, 1995; Antony, 1992). In such cases, a liposomal carrier would need to release sufficient drug near a tumor site to achieve a therapeutic effect (Heath et al., 1983; Matthay et al., 1989; Allen et al., 1992). Lastly, the use of conventional liposome formulations increases a patient's risk of acquiring opportunistic infections (White, 1997), owing to localization of drugs in reticuloendothelial system macrophages and an attendant macrophage toxicity (Allen et al., 1984; Daemen et al., 1995, 1997). This problem becomes accentuated in immune deficient patients, such as AIDS patients being treated for Kaposi's sarcoma.

Because problems continue to hamper significantly the success of cancer therapeutics, an urgent need exists for targeted drug delivery strategies that will either selectively deliver drugs to tumor cells and target organs, or protect normal tissues from administered antineoplastic agents. Such strategies should improve the efficacy of drug treatment by increasing the therapeutic indexes of anticancer agents, while minimizing the risks of drug-related toxicity.

An international patent application, PCT/IB02/04632, has described recombinant, intact minicells that contain therapeutic nucleic acid molecules. Such minicells are effective vectors for delivering oligonucleotides and polynucleotides to host cells in vitro and in vivo. Data presented in PCT/IB02/04632 demonstrated, for example, that recombinant minicells carrying mammalian gene expression plasmids can be delivered to phagocytic cells and to non-phagocytic cells. The application also described the genetic transformation of minicell-producing parent bacterial strains with heterologous nucleic acids carried on episomally-replicating plasmid DNAs. Upon separation of parent bacteria and minicells, some of the episomal DNA segregated into the minicells. The resulting recombinant minicells were readily engulfed by mammalian phagocytic cells and became degraded within intracellular phagolysosomes. Surprisingly, some of the recombinant DNA escaped the phagolysosomal membrane and was transported to the mammalian cell nucleus, where the recombinant genes were expressed. Thus, the application showed a usefulness for minicells in human and animal gene therapy.

The present invention builds on these recent discoveries relating to minicells, and addresses the continuing needs for improved drug delivery strategies, especially in the context of cancer chemotherapy.

SUMMARY OF THE INVENTION

To address these and other needs, the present invention provides, in one aspect, a composition consisting essentially of intact minicells that contain a drug, such as a cancer chemotherapy drug. In a related aspect, the invention provides a composition comprising (i) bacterially derived intact minicells and (ii) a pharmaceutically acceptable carrier therefor, where the minicells contain a drug.

According to another aspect, the invention provides a targeted drug delivery method that comprises bringing bispecific ligands into contact with (i) bacterially derived minicells that contain a desired drug and (ii) mammalian cells, preferably non-phagocytic mammalian cells. The bispecific ligands have specificity for both a surface component on the minicells and a surface component on the mammalian cells. As a result, the ligands cause the minicells to bind to the mammalian cells, the minicells are engulfed by the mammalian cells, and the drug is released into the cytoplasm of the mammalian cells.

The invention also provides bispecific ligands useful for targeting minicell vehicles to mammalian host cells. The bispecific ligand may be polypeptide, carbohydrate or glycopeptide; and may comprise an antibody or antibody fragment. In preferred embodiments, the bispecific ligand has a first arm that carries specificity for a bacterial minicell surface structure and a second arm that carries specificity for a mammalian cell surface structure. A desirable minicell surface structure for ligand binding is an O-polysaccharide component of a lipopolysaccharide. Desirable mammalian cell surface structures for ligand binding are receptors, preferably those capable of activating receptor-mediated endocytosis.

In another aspect, the invention provides a composition comprising (i) a bacterially derived minicell that contains a drug molecule and (ii) a bispecific ligand that is capable of binding to a surface component of the minicell and to a surface component of a mammalian cell.

The invention provides another drug delivery method that entails bringing bacterially derived minicells that contain a drug into contact with target mammalian cells that are phagocytosis- or endocytosis-competent. The mammalian cells engulf the drug-loaded minicells, which then release their drug payload intracellularly.

The invention further provides methodology for loading minicells with a drug. One such method involves creating a concentration gradient of the drug between an extracellular medium containing the minicells and the minicell cytoplasm. The drug naturally moves down this concentration gradient, into the minicell cytoplasm.

Another method of loading minicells with a drug involves culturing a recombinant parent bacterial cell under conditions wherein the parent bacterial cell transcribes and translates a therapeutic nucleic acid encoding the drug, such that the drug is released into the cytoplasm of the parent bacterial cell. When the parent bacterial cell divides and forms progeny minicells, the minicells also contain the drug in their cytoplasm.

Yet another method of loading minicells with a drug involves culturing a recombinant minicell that contains a therapeutic nucleic acid encoding the drug under conditions such that the therapeutic nucleic acid is transcribed and translated within the minicell.

The invention also provides for the use of bacterially derived intact minicells and bispecific ligands in preparing a medicament for use in a method of treating disease or modifying a trait by administration of the medicament to a cell, tissue or organ. In the medicament, minicells contain a drug molecule and bispecific ligands that are capable of binding to the minicells and to target mammalian cells. Such medicaments are useful to treat various conditions and diseases, including acquired diseases such as AIDS, pneumonia and tuberculosis, but are particularly useful in the context of cancer chemotherapy.

The invention affords significant improvements over conventional drug therapy techniques by (i) reducing drug-related toxicity, because the drug is specifically delivered intracellularly within target cells, (ii) alleviating drug-associated side effects at the site of administration in a human or animal, because the drug is packaged within minicells and not free to interact with non-targeted cells and tissues at the site of administration, (iii) eliminating the need for continuous infusion of drug, because a therapeutic dose of targeted and drug-packaged minicells can be administered by routine injection, (iv) reducing the effective dose of a drug, because specific targeting is achieved, and (v) sometimes eliminating the need to purify the drug, because the drug can be synthesized biologically by either the minicell drug delivery vehicle or the parent bacteria. The use of minicells for both drug biosynthesis and targeted delivery to desired mammalian cells constitutes a particular advantage, because many drugs conventionally are extracted from rare plant or marine sources, or are very difficult to synthesize chemically. Additionally, some chemotherapeutic drugs, including methotrexate, gain entry into mammalian cells via a membrane-associated active transport mechanism.

DETAILED DESCRIPTION OF THE PREFERRED EMBODIMENTS

Figure 1:
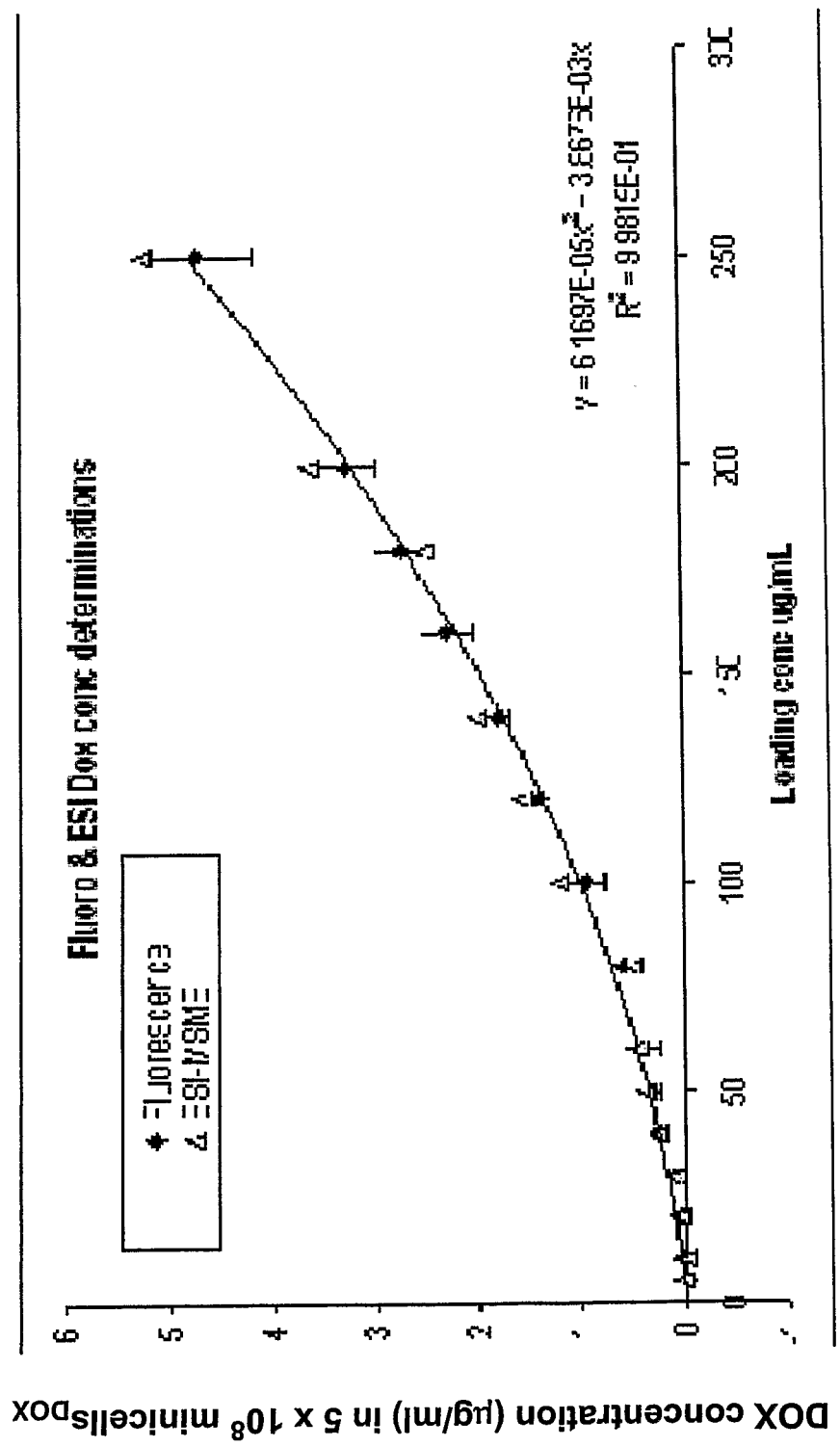
FIG. 1 is a chart showing high performance liquid chromatography (HPLC) and liquid chromatograph-mass spectrometry (LC-MS) quantitation of Doxorubicin packaged in minicells (minicells$_{DOX}$). 5×10$^8$ minicells were packaged with various concentrations of Doxorubicin in the external medium (shown on the x-axis). The minicells$_{DOX}$ were purified and the Doxorubicin was extracted using novel procedures (described in Example 3). Doxorubicin concentration in the extracts was measured using HPLC (circles) and LC-MS (triangles) and plotted on the y-axis.

The present inventors have determined that bacterially derived intact minicells are effective vehicles for packaging and delivering drugs to target mammalian cells in vitro and in vivo. More particularly, the inventors have found that a minicell carrying a drug payload can be directed to target cells, which internalize the minicell and process it such that the drug payload is released into the cytoplasm of the target cell. Surprisingly, the drug survives this process without becoming degraded.

In one example of these discoveries, the inventors observed that drug-packaged minicells can be targeted to cancer cells, internalized into the cancer cells in vitro, and degraded within late endosomes or phagolysosomes, thereby releasing therapeutically effective amounts of bioactive drug into the cancer cell cytoplasm. See the examples, below.

In a further example, these observations were corroborated by in-vivo studies using human tumor xenografts in nude mice. Intravenous delivery of drug-packaged minicells demonstrated highly significant tumor xenograft reduction in all mice (11 mice per group). See the examples, below.

Thus, the inventors have discovered (i) that a range of different drugs can be packaged into intact minicells, (ii) that drugs move one-way from the extracellular environment into the cytoplasm of intact minicells, (iii) that therapeutically significant concentrations of drugs can be transferred into the cytoplasm of intact minicells, (iv) that intact minicell membranes are impervious to drug leakage from minicell cytoplasm, (v) that attachment of bispecific ligands to surface structures of drug-packaged minicells does not destabilize the minicells and that minicells can thereby specifically bind to target mammalian cells both in-vitro and in-vivo, (vi) that phagocytosis- or endocytosis-competent mammalian cells engulf drug-packaged minicells, (vii) that non-phagocytic mammalian cells rapidly engulf surface receptor-bound drug-packaged minicells, (viii) that after engulfed minicells are degraded within vacuoles, significant amounts of bioactive drug escape the vacuolar membrane, (viii) that the escaped drug can affect its intracellular target within the mammalian cell, (ix) that chemotherapeutic drug-packaged minicells can permeate leaky vasculature surrounding tumor masses in vivo, (x) that highly significant therapeutic effects, including tumor regression and disease stabilization, can be achieved using chemotherapeutic drug-packaged minicells, and (xi) that drug-packaged minicells significantly reduce or eliminate unwanted toxicity.

The ability of minicells to package drugs is surprising for several reasons. It is surprising that that intact minicell membranes are permeable to a range of structurally dissimilar hydrophilic, hydrophobic and amphipatic drugs. By contrast, live bacterial cells exhibit selective membrane permeability to solutes, so it appears that minicells have lost this selectivity. It also is surprising that minicells are unable to expel drugs from their cytoplasm, because live bacterial cells extrude noxious chemicals that enter into the bacterial cytoplasm. Even against a reverse osmotic gradient, in which drug-loaded minicells are suspended in phosphate-buffered saline containing no drug, minicells retain drug. This is additionally surprising because drugs appear simply to diffuse into minicells through intact minicell membranes, yet the diffusion channels are not available for drugs to diffuse out of minicells. Another unexpected aspect of the present invention is that therapeutically significant drug concentrations can be packaged within minicells, because bacterial cytoplasm (and, hence, minicell cytoplasm) contains significant concentrations of biocompatible solutes. Thus, it was believed that there might be insufficient spare intracellular space to accommodate high concentrations of non-biocompatible drug solutes, without loss of minicell integrity.

The ability of minicells to deliver drugs also is surprising for several reasons. It is unexpected, for example, that drug-packaged minicells do not leak drug into the extracellular space. This is a persistent problem with liposomal drug delivery vectors, and minicells, like liposomes, are non-living vesicles. Nevertheless, although intact minicell membranes lack selectivity to drug permeation, the membrane integrity is sufficient to prevent leakage of intracellular solutes. Also surprising, and unlike liposomal drug delivery vectors, attachment of ligands to the surface of drug-packaged minicells does not cause destabilization of minicell integrity or membrane perturbations that result in drug leakage. Further, it is unexpected that drug-packaged minicells are endocytosed rapidly by non-phagocytic mammalian cells, simply by virtue of a bispecific ligand linking the two. It was widely believed heretofore that large particles, like bacteria, can only penetrate and invade non-phagocytic mammalian cells via an active process involving secretion of invasion-associated proteins by a live pathogen. Minicells are non-living vesicles lacking the ability to actively invade non-phagocytic mammalian cells. Yet another surprise was that drug-packaged minicells carrying a bispecific ligand are able to extravasate tumor neovasculature in vivo. While there is considerable debate regarding the leakiness of tumor mincroenvironment neovasculature, the current view is that pores in the neovasculature are 150-400 nm in diameter (Gabizon et al., 2003). Minicells carrying a surface ligand, however, are 400 nm to 600 nm in diameter, yet still are able to extravasate tumor neovasculature in-vivo. The ability of drugs packaged in minicells to avoid degradation also is surprising for several reasons. Engulfed minicells are subjected to lysosomal and late-endosomal environments known to be harsh, and which break down minicells. Despite the harshness of these environments, the inventors observed that a range of drugs are released from minicells in a biologically active form and remain significantly unaltered. Perhaps even more surprising was the discovery that a significant concentration of drug is able to escape, in its active form, into the mammalian cell cytoplasm. Pursuant to the present invention, that is, drug concentrations within mammalian cells are sufficient to work a therapeutic effect in both in vitro and in vivo experiments.

Yet another surprising discovery is that drug-packaged minicells minimize adverse side effects. For example, at the site of intravenous injection in the tail vein of nude mice, free drug injections cause severe skin reactions, whereas drug-packaged minicells do not cause such an adverse side effect.

In accord with these discoveries, the invention provides a composition consisting essentially of intact minicells that contain a desired drug, such as a cancer chemotherapy drug. The invention also provides a composition comprising (i) bacterially derived intact minicells and (ii) a pharmaceutically acceptable carrier therefor, where the minicells contain a drug, such as a cancer chemotherapy drug.

Minicells of the invention are anucleate forms of *E. coli* or other bacterial cells, engendered by a disturbance in the coordination, during binary fission, of cell division with DNA segregation. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an anucleate minicell. See de Boer et al., 1992; Raskin & de Boer, 1999; Hu & Lutkenhaus, 1999; Harry, 2001. Minicells are distinct from other small vesicles that are generated and released spontaneously in certain situations and, in contrast to minicells, are not due to specific genetic rearrangements or episomal gene expression. For practicing the present invention, it is desirable for minicells to have intact cell walls ("intact minicells").

In addition to min operon mutations, anucleate minicells also are generated following a range of other genetic rearrangements or mutations that affect septum formation, for example in the divIVB1 in *B. subtilis*. See Reeve and Cornett, 1975; Levin et al., 1992. Minicells also can be formed following a perturbation in the levels of gene expression of proteins involved in cell division/chromosome segregation. For example, overexpression of minE leads to polar division and production of minicells. Similarly, chromosome-less minicells may result from defects in chromosome segregation for example the smc mutation in *Bacillus subtilis* (Britton et al., 1998), spoOJ deletion in *B. subtilis* (Ireton et al., 1994), mukB mutation in *E. coli* (Hiraga et al., 1989), andparC mutation in *E. coli* (Stewart and D'Ari, 1992). Gene products may be supplied in trans. When over-expressed from a high-copy number plasmid, for example, CafA may enhance the rate of cell division and/or inhibit chromosome partitioning after replication (Okada et al., 1994), resulting in formation of chained cells and anucleate minicells (Wachi et al., 1989; Okada et al., 1993). Minicells can be prepared from any bacterial cell of Gram-positive or Gram-negative origin.

Minicells of the invention contain one or more drugs. The term "drug" includes any physiologically or pharmacologically active substance that produces a local or systemic effect in animals, particularly mammals and humans. Drugs may be inorganic or organic compounds, without limitation, including peptides, proteins, nucleic acids, and small molecules, any of which may be characterized or uncharacterized. They may be in various forms, such as unchanged molecules, molecular complexes, pharmacologically acceptable salts, such as hydrochloride, hydrobromide, sulfate, laurate, palmitate, phosphate, nitrite, nitrate, borate, acetate, maleate, tartrate, oleate, salicylate, and the like. For acidic drugs, salts of metals, amines or organic cations, for example, quaternary ammonium, can be used. Derivatives of drugs, such as bases, esters and amides also can be used. A drug that is water insoluble can be used in a form that is a water soluble derivative thereof, or as a base derivative thereof, which in either instance, or by its delivery, is converted by enzymes, hydrolyzed by the body pH, or by other metabolic processes to the original therapeutically active form.

Drugs having any physiological or pharmacological activity are useful in this invention, but cancer chemotherapy agents are preferred drugs. Useful cancer chemotherapy drugs include nitrogen mustards, nitrosoruneas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Minicell-containing compositions of this invention preferably contain fewer than about 1 contaminating parent bacterial cell per $10^7$ minicells, more preferably contain fewer than about 1 contaminating parent bacterial cell per $10^8$ minicells, even more preferably contain fewer than about 1 contaminating parent bacterial cell per $10^9$ minicells, still more preferably contain fewer than about 1 contaminating parent bacterial cell per $10^{10}$ minicells and most preferably contain fewer than about 1 contaminating parent bacterial cell per $10^{11}$ minicells.

Methods of purifying minicells are known in the art and described in PCT/IB02/04632. One such method combines cross-flow filtration (feed flow is parallel to a membrane surface; Forbes, 1987) and dead-end filtration (feed flow is perpendicular to the membrane surface). Optionally, the filtration combination can be preceded by a differential centrifugation, at low centrifugal force, to remove some portion of the bacterial cells and thereby enrich the supernatant for minicells.

Another purification method employs density gradient centrifugation in a biologically compatible medium. After centrifugation, a minicell band is collected from the gradient, and, optionally, the minicells are subjected to further rounds of density gradient centrifugation to maximize purity. The method may further include a preliminary step of performing differential centrifugation on the minicell-containing sample. When performed at low centrifugal force, differential centrifugation will remove some portion of parent bacterial cells, thereby enriching the supernatant for minicells.

Particularly effective purification methods exploit bacterial filamentation to increase minicell purity. Thus a minicell purification method can include the steps of (a) subjecting a sample containing minicells to a condition that induces parent bacterial cells to adopt a filamentous form, followed by (b) filtering the sample to obtain a purified minicell preparation.

Known minicell purification methods also can be combined. One highly effective combination of methods is as follows:

Step A: Differential centrifugation of a minicell producing bacterial cell culture. This step, which may be performed at 2000 g for about 20 minutes, removes most parent bacterial cells, while leaving minicells in the supernatant.

Step B: Density gradient centrifugation using an isotonic and non-toxic density gradient medium. This step separates minicells from many contaminants, including parent bacterial cells, with minimal loss of minicells. Preferably, this step is repeated within a purification method.

Step C: Cross-flow filtration through a 0.45 µm filter to further reduce parent bacterial cell contamination.

Step D: Stress-induced filamentation of residual parent bacterial cells. This may be accomplished by subjecting the minicell suspension to any of several stress-inducing environmental conditions.

Step E: Antibiotic treatment to kill parent bacterial cells.

Step F: Cross-flow filtration to remove small contaminants, such as membrane blebs, membrane fragments, bacterial debris, nucleic acids, media components and so forth, and to concentrate the minicells. A 0.2 µm filter may be employed to separate minicells from small contaminants, and a 0.1 µm filter may be employed to concentrate minicells.

Step G: Dead-end filtration to eliminate filamentous dead bacterial cells. A 0.45 µm filter may be employed for this step.

Step H: Removal of endotoxin from the minicell preparation. Anti-Lipid A coated magnetic beads may be employed for this step.

In another aspect, the invention provides a targeted drug delivery method that comprises bringing bispecific ligands into contact with (i) bacterially derived minicells that contain a drug molecule and (ii) mammalian cells. The bispecific ligands, having specificity for both minicell and mammalian cell components, cause the minicells to bind to the mammalian cells, such that the minicells are engulfed by the mammalian cells, and the drug is released into the cytoplasm of the mammalian cells.

The inventors found that this approach is broadly applicable to a range of mammalian cells, including cells that normally are refractory to specific adhesion and endocytosis of minicells. For example, bispecific antibody ligands with anti-O-polysaccharide specificity on one arm and anti-HER2 receptor, anti-EGF receptor or anti-androgen receptor specificity on the other arm efficiently bind minicells to the respective receptors on a range of target non-phagocytic cells. These cells include lung, ovarian, brain, breast, prostate and skin cancer cells. Moreover, the efficient binding precedes rapid endocytosis of the minicells by each of the non-phagocytic cells.

Target cells of the invention include any cell into which a drug is to be introduced. "Introduced," when used in reference to a drug, means that the drug carried within a minicell is delivered to the target cell, preferably intracellularly. Desirable target cells are characterized by expression of a cell surface receptor that, upon binding of a ligand, facilitates endocytosis. Preferred target cells are non-phagocytic, meaning that the cells are not professional phagocytes, such as macrophages, dendritic cells and Natural Killer (NK) cells. Preferred target cells also are mammalian.

Ligands useful in the targeted drug delivery methods of this invention include any agent that binds to a surface component on a target cell and to a surface component on a minicell. Preferably, the surface component on a target cell is a receptor, especially a receptor capable of mediating endocytosis. The ligands may comprise a polypeptide and/or carbohydrate component. Antibodies are preferred ligands. For example, a bispecific antibody that carries dual specificities for a surface component on bacterially derived intact minicells and for a surface component on target mammalian cells, can be used efficiently to target the minicells to the target mammalian cells in vitro and in vivo. Useful ligands also include receptors, enzymes, binding peptides, fusion/chimeric proteins and small molecules.

The selection of a particular ligand is made on two primary criteria: (i) specific binding to one or more domains on the surface of intact minicells and (ii) specific binding to one or more domains on the surface of the target cells. Thus, ligands preferably have a first arm that carries specificity for a bacterially derived intact minicell surface structure and a second arm that carries specificity for a mammalian cell surface structure. Each of the first and second arms may be multivalent. Preferably, each arm is monospecific, even if multivalent.

For binding to bacterially derived minicells, it is desirable for one arm of the ligand to be specific for the O-polysaccharide component of a lipopolysaccharide found on the parent bacterial cell. Other minicell surface structures that can be exploited for ligand binding include cell surface-exposed polypeptides and carbohydrates on outer membranes, such as pilli, fimbrae and flagella cell surface exposed peptide segments.

For binding to target cells, one arm of the ligand is specific for a surface component of a mammalian cell. Such components include cell surface proteins, peptides and carbohydrates, whether characterized or uncharacterized. Cell surface receptors, especially those capable of activating receptor-mediated endocytosis, are desirable cell surface components for targeting. Such receptors, if over-expressed on the target cell surface, confer additional selectivity for targeting the cells to be treated, thereby reducing the possibility for delivery to non-target cells.

By way of example, one may target tumor cells, metastatic cells, vasculature cells, such as endothelial cells and smooth muscle cells, lung cells, kidney cells, blood cells, bone marrow cells, brain cells, liver cells, and so forth, or precursors of any selected cell by selecting a ligand that specifically binds a cell surface receptor motif on the desired cells. Examples of cell surface receptors include carcinoembryonic antigen (CEA), which is overexpressed in most colon, rectum, breast, lung, pancreas and gastrointestinal tract carcinomas (Marshall, 2003); heregulin receptors (HER-2, neu or c-erbB-2), which is frequently overexpressed in breast, ovarian, colon, lung, prostate and cervical cancers (Hung et al., 2000); epidermal growth factor receptor (EGFR), which is highly expressed in a range of solid tumors including those of the breast, head and neck, non-small cell lung and prostate (Salomon et al., 1995); asialoglycoprotein receptor (Stockert, 1995); transferrin receptor (Singh, 1999); serpin enzyme complex receptor, which is expressed on hepatocytes (Ziady et al., 1997); fibroblast growth factor receptor (FGFR), which is overexpressed on pancreatic ductal adenocarcinoma cells (Kleeff et al., 2002); vascular endothelial growth factor receptor (VEGFR), for anti-angiogenesis gene therapy (Becker et al., 2002 and Hoshida et al., 2002); folate receptor, which is selectively overexpressed in 90% of nonmucinous ovarian carcinomas (Gosselin and Lee, 2002); cell surface glycocalyx (Batra et al., 1994); carbohydrate receptors (Thurnher et al., 1994); and polymeric immunoglobulin receptor, which is useful for gene delivery to respiratory epithelial cells and attractive for treatment of lung diseases such as Cystic Fibrosis (Kaetzel et al., 1997).

In a further example, anti-viral, anti-microbial and anti-parasitic drugs can be incorporated into intact minicells and targeted delivery of the drugs can be achieved to specific infected cells, such as HIV-infected helper CD4+ T-lymphocytes.

Preferred ligands comprise antibodies and/or antibody derivatives. As used herein, the term "antibody" encompasses an immunoglobulin molecule obtained by in vitro or in vivo generation of an immunogenic response. The term "antibody" includes polyclonal, monospecific and monoclonal antibodies, as well as antibody derivatives, such as single-chain antibody fragments (scFv). Antibodies and antibody derivatives useful in the present invention also may be obtained by recombinant DNA techniques.

Wild type antibodies have four polypeptide chains, two identical heavy chains and two identical light chains. Both types of polypeptide chains have constant regions, which do not vary or vary minimally among antibodies of the same class, and variable regions. Variable regions are unique to a particular antibody and comprise an antigen binding domain that recognizes a specific epitope. The regions of the antigen binding domain that are most directly involved in antibody binding are "complementarity-determining regions" (CDRs).

The term "antibody" also encompasses derivatives of antibodies, such as antibody fragments that retain the ability to specifically bind to antigens. Such antibody fragments include Fab fragments (a fragment that contains the antigen-binding domain and comprises a light chain and part of a heavy chain bridged by a disulfide bond), Fab' (an antibody fragment containing a single antigen-binding domain comprising a Fab and an additional portion of the heavy chain through the hinge region, F(ab')2 (two Fab' molecules joined by interchain disulfide bonds in the hinge regions of the heavy chains), a bispecific Fab (a Fab molecule having two antigen binding domains, each of which may be directed to a different epitope), and an scFv (the variable, antigen-binding determinative region of a single light and heavy chain of an antibody linked together by a chain of amino acids.)

When antibodies, including antibody fragments, constitute part or all of the ligands, they preferably are of human origin or are modified to be suitable for use in humans. So-called "humanized antibodies" are well known in the art. See, e.g., Osbourn et al., 2003. They have been modified by genetic manipulation and/or in vitro treatment to reduce their antigenicity in a human. Methods for humanizing antibodies are described, e.g., in U.S. Pat. No. 6,639,055, No. 5,585,089, and No. 5,530,101. In the simplest case, humanized antibodies are formed by grafting the antigen-binding loops, known as complementarity-determining regions (CDRs), from a mouse mAb into a human IgG. See Jones et al., 1986; Riechmann et al., 1988; and Verhoeyen et al., 1988. The generation of high-affinity humanized antibodies, however, generally requires the transfer of one or more additional residues from the so-called framework regions (FRs) of the mouse parent mAb. Several variants of the humanization technology also have been developed. See Vaughan et al., 1998.

Human antibodies, rather than "humanized antibodies," also may be employed in the invention. They have high affinity for their respective antigens and are routinely obtained from very large, single-chain variable fragments (scFvs) or Fab phage display libraries. See Griffiths et al., 1994; Vaughan et al., 1996; Sheets et al., 1998; de Haard et al., 1999; and Knappik et al., 2000.

Useful ligands also include bispecific single chain antibodies, which typically are recombinant polypeptides consisting of a variable light chain portion covalently attached through a linker molecule to a corresponding variable heavy chain portion. See U.S. Pat. Nos. 5,455,030; 5,260,203 and 4,496,778. Bispecific antibodies also can be made by other methods. For example, chemical heteroconjugates can be created by chemically linking intact antibodies or antibody fragments of different specificities. See Karpovsky et al., 1984. However, such heteroconjugates are difficult to make in a reproducible manner and are at least twice as large as normal monoclonal antibodies. Bispecific antibodies also can be created by disulfide exchange, which involves enzymatic cleavage and reassociation of the antibody fragments. See Glennie et al., 1987.

Because Fab and scFv fragments are monovalent they often have low affinity for target structures. Therefore, preferred ligands made from these components are engineered into dimeric, trimeric or tetrameric conjugates to increase functional affinity. See Tomlinson and Holliger, 2000; Carter, 2001; Hudson and Souriau, 2001; and Todorovska et al., 2001. Such conjugate structures may be created by chemical and/or genetic cross-links.

Bispecific ligands of the invention preferably are monospecific at each end, i.e., specific for a single component on minicells at one end and specific for a single component on target cells at the other end. The ligands may be multivalent at one or both ends, for example, in the form of so-called diabodies, triabodies and tetrabodies. See Hudson and Souriau, 2003. A diabody is a bivalent dimer formed by a non-covalent association of two scFvs, which yields two Fv binding sites. Likewise, a triabody results from the formation of a trivalent trimer of three scFvs, yielding three binding sites, and a tetrabody results from the formation of a tetravalent tetramer of four scFvs, yielding four binding sites.

Several humanized, human, and mouse monoclonal antibodies and fragments thereof that have specificity for receptors on mammalian cells have been approved for human therapeutic use, and the list is growing rapidly. See Hudson and Souriau, 2003. An example of such an antibody that can be used to form one arm of a bispecific ligand has specificity for HER2: Herceptin™; Trastuzumab.

Antibody variable regions also can be fused to a broad range of protein domains. Fusion to human immunoglobulin domains such as IgG1 CH3 both adds mass and promotes dimerization. See Hu et al., 1996. Fusion to human Ig hinge-Fc regions can add effector functions. Also, fusion to heterologous protein domains from multimeric proteins promotes multimerization. For example, fusion of a short scFv to short amphipathic helices has been used to produce miniantibodies. See Pack and Pluckthun, 1992. Domains from proteins that form heterodimers, such as fos/jun, can be used to produce bispecific molecules (Kostelny et al., 1992) and, alternately, homodimerization domains can be engineered to form heterodimers by engineering strategies such as "knobs into holes" (Ridgway et al., 1996). Finally, fusion protein partners can be selected that provide both multimerization as well as an additional function, e.g. streptavidin. See Dubel et al., 1995.

In another aspect, the invention provides a composition of matter useful for introducing drug molecules into target mammalian cells with high efficiency. The composition comprises (i) a bacterially derived minicell and (ii) a bispecific ligand. The minicell and ligand may be any of those described herein. Thus, the minicell contains a drug and the bispecific ligand preferably is capable of binding to a surface component of the minicell and to a surface component of a target mammalian cell.

A composition consisting essentially of minicells and bispecific ligands of the present invention (that is, a composition that includes such minicells and ligands with other constituents that do not interfere unduly with the drug-delivering quality of the composition) can be formulated in conventional manner, using one or more pharmaceutically acceptable carriers or excipients.

The term "pharmaceutically acceptable" means that a carrier or excipient does not abrogate biological activity of the composition being administered, is chemically inert and is not toxic to the organism in which it is administered. Formulations may be presented in unit dosage form, e.g., in ampules or vials, or in multi-dose containers, with or without an added preservative. The formulation can be a solution, a suspension, or an emulsion in oily or aqueous vehicles, and may contain formulatory agents, such as suspending, stabilizing and/or dispersing agents. A suitable solution is isotonic with the blood of the recipient and is illustrated by saline, Ringer's solution, and dextrose solution. Alternatively, compositions may be in lyophilized powder form, for reconstitution with a suitable vehicle, e.g., sterile, pyrogen-free water or physiological saline. The compositions also may be formulated as a depot preparation. Such long-acting formulations may be administered by implantation (for example, subcutaneously or intramuscularly) or by intramuscular injection.

A composition of the present invention can be administered via various routes and to various sites in a mammalian body, to achieve the therapeutic effect(s) desired, either locally or systemically. Delivery may be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The mode and site of administration is dependent on the location of the target cells. For example, cysticfibrotic cells may be efficiently targeted by inhaled delivery of the targeted recombinant minicells. Similarly, tumor metastasis may be more efficiently treated via intravenous delivery of targeted recombinant minicells. Primary ovarian cancer may be treated via intraperitoneal delivery of targeted recombinant minicells.

The present invention further provides for drug delivery by means of bringing bacterially derived minicells, which contain a drug, into contact with mammalian cells that are phagocytosis- or endocytosis-competent. Such mammalian cells, which are capable of engulfing parent bacterial cells in the manner of intracellular bacterial pathogens, likewise engulf the minicells, which release their drug payload into the cytoplasm of the mammalian cells. This drug-delivery approach can be effected without the use a targeting ligands.

A variety of mechanisms may be involved in the engulfing of minicells by a given type of cell, and the present invention is not dependent on any particular mechanism in this regard. For example, phagocytosis is a well-documented process in which macrophages and other phagocyte cells, such as neutrophils, ingest particles by extending pseudopodia over the particle surface until the particle is totally enveloped. Although described as "non-specific" phagocytosis, the involvement of specific receptors in the process has been demonstrated. See Wright & Jong (1986); Speert et al. (1988).

Thus, one form of phagocytosis involves interaction between surface ligands and ligand-receptors located at the membranes of the pseudopodia (Shaw and Griffin, 1981). This attachment step, mediated by the specific receptors, is thought to be dependent on bacterial surface adhesins. With respect to less virulent bacteria, such as non-enterotoxigenic *E. coli*, phagocytosis also may occur in the absence of surface ligands for phagocyte receptors. See Pikaar et al. (1995), for instance. Thus, the present invention encompasses but is not limited to the use of minicells that either possess or lack surface adhesins, in keeping with the nature of their parent bacterial cells, and are engulfed by phagocytes (i.e., "phagocytosis-competent" host cells), of which neutrophils and macrophages are the primary types in mammals.

Another engulfing process is endocytosis, by which intracellular pathogens exemplified by species of *Salmonella, Escherichia, Shigella, Helicobacter, Pseudomonas* and *Lactobacilli* gain entry to mammalian epithelial cells and replicate there. Two basic mechanisms in this regard are Clathrin-dependent receptor-mediated endocytosis, also known as "coated pit endocytosis" (Riezman, 1993), and Clathrin-independent endocytosis (Sandvig & Deurs, 1994). Either or both may be involved when an engulfing-competent cell that acts by endocytosis (i.e., an "endocytosis-competent" host cell) engulfs minicells in accordance with the invention. Representative endocytosis-competent cells are breast epithelial cells, enterocytes in the gastrointestinal tract, stomach epithelial cells, lung epithelial cells, and urinary tract and bladder epithelial cells.

When delivering a drug to an engulfing-competent mammalian cell without the use of a targeting ligand, the nature of the application contemplated will influence the choice of bacterial source for the minicells employed. For example, *Salmonella, Escherichia* and *Shigella* species carry adhesins that are recognized by endocytosis-mediating receptors on enterocytes in the gastrointestinal tract, and may be suitable to deliver a drug that is effective for colon cancer cells. Similarly, minicells derived from *Helicobacter pylori*, carrying adhesins specific for stomach epithelial cells, could be suited for delivery aimed at stomach cancer cells. Inhalation or insufflation may be ideal for administering intact minicells derived from a *Pseudomonas* species that carry adhesins recognized by receptors on lung epithelial cells. Minicells derived from *Lactobacilli* bacteria, which carry adhesins specific for urinary tract and bladder epithelial cells, could be well-suited for intraurethral delivery of a drug to a urinary tract or a bladder cancer. The invention also provides for the use of bacterially derived intact minicells and bispecific ligands in preparing medicament for use in a method of treating disease or modifying a trait by administration of the medicament to a cell, tissue or organ. In the medicament, minicells contain a drug molecule and bispecific ligands are capable of binding to the minicells and to target mammalian cells. Such medicaments are useful to treat various conditions and diseases, including acquired diseases such as AIDS, pneumonia and tuberculosis, but are particularly useful in the context of cancer chemotherapy.

The invention further provides methods of loading minicells with a drug. Using these methods, drug packaging can be accomplished for both hydrophilic and hydrophobic drugs. One method of loading minicells with a drug involves creating a concentration gradient of the drug between an extracellular medium containing the minicells and the minicell cytoplasm. When the extracellular medium contains a higher drug concentration than the minicell cytoplasm, the drug naturally moves down this concentration gradient, into the minicell cytoplasm. When the concentration gradient is reversed, however, the drug does not move out of the minicells.

That therapeutically significant amounts of drugs can be packaged thusly in non-living minicells without leakage is surprising for several reasons. It is known that the outer envelope of live bacteria, both Gram-negative and Gram-positive, forms an effective barrier to solutes in the surrounding medium, while being permeable to water. This protects the bacteria from deleterious effects of toxic molecules, such as biocides and antibiotics. It is also known that the bacterial envelope confers intrinsic resistance to the passive diffusion and intracellular entry of hydrophobic chemicals that cannot enter through water filled hydrophilic channels, formed by membrane-associated proteins called porins.

Minicells contain the same outer envelope as their parent bacterial cells. Thus, it is surprising that both hydrophilic drugs, exemplified by Doxorubicin and Vinblastine, and hydrophobic drugs, exemplified by Paclitaxel, can be readily transferred into the minicell cytoplasm by creating a simple concentration gradient of the drug between the extra-minicell and intra-minicell environments. This suggests that the envelope permeability of non-living bacteria and their derivatives is quite different from the envelope permeability of living bacteria.

The discovery that drug movement occurs only in one direction in minicells was a greater surprise. It is well established that live bacteria have active efflux processes to remove toxic chemical entities that happen to enter their cytoplasm (reviewed by Borges-Walmsley and Walmsley, 2001). These processes are mediated by multidrug transporters, a large and diverse group of proteins capable of protecting cells against a wide variety of environmental toxins by active extrusion of noxious compounds. There are at least five known families, based on sequence similarity, of multidrug transporters. They include the (i) major facilitator (MFS), (ii) resistance-nodulation-cell division (RND), (iii) small multidrug resistance, (iv) multidrug and toxic compound extrusion, and (v) ATP-binding cassette families. These multidrug transporters are bacterial membrane bound proteins and are widely distributed in bacterial species.

Multidrug transporters should be conserved in minicell membranes, yet they surprisingly appear to be non-functional, possibly because minicells are non-living and lack the ATP necessary to drive multidrug transporters.

To load minicells with drugs that normally are not water soluble, the drugs initially can be dissolved in an appropriate solvent. For example, Paclitaxel can be dissolved in a 1:1 blend of ethanol and cremophore EL (polyethoxylated castor oil), followed by a dilution in PBS to achieve a solution of Paclitaxel that is partly diluted in aqueous media and carries minimal amounts of the organic solvent to ensure that the drug remains in solution. Minicells can be incubated in this final medium for drug loading. Thus, the inventors discovered that even hydrophobic drugs can diffuse into the cytoplasm of minicells to achieve a high and therapeutically significant cytoplasmic drug load. This is unexpected because the minicell membrane is composed of a hydrophobic phospholipid bilayer, which would be expected to prevent diffusion of hydrophobic molecules into the cytoplasm.

Another method of loading minicells with a drug involves culturing a recombinant parent bacterial cell under conditions wherein the parent bacterial cell transcribes and translates a therapeutic nucleic acid encoding the drug, such that the drug is released into the cytoplasm of the parent bacterial cell. For example, a gene cluster encoding the cellular biosynthetic pathway for a desired drug can be cloned and transferred into a parent bacterial strain that is capable of producing minicells. Genetic transcription and translation of the gene cluster results in biosynthesis of the drug within the cytoplasm of the parent bacterial cells, filling the bacterial cytoplasm with the drug. When the parent bacterial cell divides and forms progeny minicells, the minicells also contain the drug in their cytoplasm. The pre-packaged minicells can be purified by any of the minicell purification processes known in the art and described above.

Similarly, another method of loading minicells with a drug involves culturing a recombinant minicell that contains an expression plasmid encoding the drug under conditions such that the gene encoding the drug is transcribed and translated within the minicell.

For producing drugs directly within parent bacterial cells or minicells, the parent bacterial cells or minicells contain a nucleic acid molecule that, upon transcription and/or translation, function to ameliorate or otherwise treat a disease or modify a trait in a cell, tissue or organ. For purposes of the present description, such nucleic acid molecules are categorized as "therapeutic nucleic acid molecules." Ordinarily, the therapeutic nucleic acid is found on a plasmid within the parent bacteria or minicells.

The therapeutic nucleic acid molecule encodes a drug product, such as functional RNA (e.g., antisense or siRNA) or a peptide, polypeptide or protein, the production of which is desired. For example, the genetic material of interest can encode a hormone, receptor, enzyme, or (poly) peptide of therapeutic value. A therapeutic nucleic acid molecule may be the normal counterpart of a gene that expresses a protein that functions abnormally or that is present in abnormal levels in a disease state, as is the case, for example, with the cystic fibrosis transmembrane conductance regulator in cystic fibrosis (Kerem et al., 1989; Riordan et al., 1989; Rommens et al., 1989), with β-globin in sickle-cell anemia, and with any of α-globin, β-globin and γ-globin in thalassemia. The therapeutic nucleic acid molecule can have an antisense RNA transcript or small interfering RNA, as mentioned above.

In the treatment of cancer, a therapeutic nucleic acid molecule suitable for use according to the present invention could have a sequence that corresponds to or is derived from a gene that is associated with tumor suppression, such as the p53 gene, the retinoblastoma gene, and the gene encoding tumor necrosis factor. A wide variety of solid tumors—cancer, papillomas, and warts—should be treatable by this approach, pursuant to the invention. Representative cancers in this regard include colon carcinoma, prostate cancer, breast cancer, lung cancer, skin cancer, liver cancer, bone cancer, ovary cancer, pancreas cancer, brain cancer, head and neck cancer, and lymphoma. Illustrative papillomas are squamous cell papilloma, choroid plexus papilloma and laryngeal papilloma. Examples of wart conditions are genital warts, plantar warts, epidermodysplasia verruciformis, and malignant warts.

A therapeutic nucleic acid molecule for the present invention also can comprise a DNA segment coding for an enzyme that converts an inactive prodrug into one or more cytotoxic metabolites so that, upon in vivo introduction of the prodrug, the target cell in effect is compelled, perhaps with neighboring cells as well, to commit suicide. Preclinical and clinical applications of such a "suicide gene," which can be of non-human origin or human origin, are reviewed by Spencer (2000), Shangara et al. (2000) and Yazawa et al. (2002). Illustrative of suicide genes of non-human origin are those that code for HSV-thymidine kinase (tk), cytosine deaminase (CDA)+uracil phophoribosytransferase, xanthine-guanine phophoribosyl-transferase (GPT), nitroreductase (NTR), purine nucleoside phophrylase (PNP, DeoD), cytochrome P450 (CYP4B1), carboxypeptidase G2 (CPG2), and D-amino acid oxidase (DAAO), respectively. Human-origin suicide genes are exemplified by genes that encode carboxypeptidase A1 (CPA), deoxycytidine kinase (dCK), cytochrome P450 (CYP2B1,6), LNGFR/FKBP/Fas, FKBP/Caspases, and ER/p53, respectively.

According to the invention, the therapeutic nucleic acid typically is contained on a plasmid within the parent bacterial cell or minicell. The plasmid also may contain an additional nucleic acid segment that functions as a regulatory element, such as a promoter, a terminator, an enhancer or a signal sequence, and that is operably linked to the therapeutic nucleic acid segment.

A plasmid within a parent bacterial cell or minicell of the invention also may contain a reporter element. A reporter element confers on its recombinant host a readily detectable phenotype or characteristic, typically by encoding a polypeptide, not otherwise produced by the host, that can be detected, upon expression, by histological or in situ analysis, such as by in vivo imaging techniques. For example, a reporter element delivered by an intact minicell, according to the present invention, could code for a protein that produces, in the engulfing host cell, a colorimetric or fluorometric change that is detectable by in situ analysis and that is a quantitative or semi-quantitative function of transcriptional activation. Illustrative of these proteins are esterases, phosphatases, proteases and other enzymes, the activity of which generates a detectable chromophore or fluorophore.

Preferred examples are $E.\ coli$ β-galactosidase, which effects a color change via cleavage of an indigogenic substrate, indolyl-β-D-galactoside, and a luciferase, which oxidizes a long-chain aldehyde (bacterial luciferase) or a heterocyclic carboxylic acid (luciferin), with the concomitant release of light. Also useful in this context is a reporter element that encodes the green fluorescent protein (GFP) of the jellyfish, $Aequorea\ victoria$, as described by Prasher et al. (1995). The field of GFP-related technology is illustrated by two published PCT applications, WO 095/21191 (discloses a polynucleotide sequence encoding a 238 amino-acid GFP apoprotein, containing a chromophore formed from amino acids 65 through 67) and WO 095/21191 (discloses a modification of the cDNA for the apopeptide of $A.\ victoria$ GFP, providing a peptide having altered fluorescent properties), and by a report of Heim et al. (1994) of a mutant GFP, characterized by a 4-to-6-fold improvement in excitation amplitude.

The following examples illustrate provide a more complete understanding of the invention and are illustrative only.

Example 1

Efficient Packaging of the Hydrophilic Cancer Chemotherapeutic Drugs Doxorubicin and Vinblastine in Bacterially Derived Intact Minicells This example demonstrates that hydrophilic drugs can be packaged into the cytoplasm of bacterially derived intact minicells.

Doxorubicin is a strong antimitogenic anthracycline antibiotic isolated from $Streptomyces\ peucetius$, and is commonly employed for treating breast carcinoma (Henderson et al., 1989; Cowan et al., 1991; Chan et al., 1999; Paridaens et al., 2000; Norris et al., 2000). Even with the availability of taxanes and other new agents, Doxorubicin remains a mainstay of treatment for patients with metastatic disease.

Vinca alkaloids constitute a chemical class of major interest in cancer chemotherapy. The lead compounds, Vinblastine and Vincristine, have been employed in clinical practice for more than thirty years and remain widely used to this day. Vinblastine inhibits cell proliferation by capping microtubule ends, thereby suppressing mitotic spindle microtubule dynamics.

Minicells were obtained from an $S.\ typhimurium$ minCDE-mutant strain generated previously, as described in international application No. PCT/IB02/04632, and were purified via a gradient centrifugation/filamentation/filtration/endotoxin removal procedure described above.

Drug was packaged into the minicells by creating a concentration gradient of the drug between the extracellular and intracellular compartments. Drug moved down this gradient and into the minicell cytoplasm, through the intact minicell membrane.

The purified minicells were packaged with chemotherapeutic drug Doxorubicin (Sigma Chemical Company, St. Louis, Mo., USA) as follows. $7 \times 10^9$ minicells in BSG solution were centrifuged, the supernatant was discarded and the minicells were resuspended in 940 ul BSG and 60 ul of Doxorubicin solution (1 mg/ml; dissolved in sterile distilled water). The suspension was incubated overnight at 37° C. with rotation to allow the Doxorubicin to diffuse into the minicell cytoplasm. Excess Doxorubicin non-specifically attached to the outer surface of the minicells was then washed away by stirred cell ultrafiltration as follows. Amicon stirred ultrafiltration cell Model 8010 (Millipore, Billerica, Mass., USA) was assembled according to the manufacturer's instructions with an ultrafiltration membrane disc (polyethersulfone; molecular weight cut-off of 300 kDa; Millipore). The cell was washed three times with sterile distilled water followed by a further three washes with BSG. The cell was then filled with 9 ml of fresh BSG and the 1 ml solution of Doxorubicin-packaged minicells was added. The cell was kept under a pressure of 10 psi, stirred until the volume was reduced to 5 ml and topped-off with 5 ml BSG. Ultrafiltration was continued until the volume again dropped to 5 ml. This topping-off/ultrafiltration procedure was performed 6 times to enable a thorough washing of the exterior surfaces of the Doxorubicin-packaged minicells. During the last ultrafiltration, the volume was reduced to 1 ml and the sample was transferred to a sterile Eppendorf centrifuge tube, followed by centrifugation at 13,200 rpm for 10 minutes to pellet the Doxorubicin-packaged minicells.

Doxorubicin-packaged minicells were mounted on glass slides and were visualized using a fluorescence microscope (Leica model DM LB light microscope, 100× magnification; Leica Microsystems, Germany) because Doxorubicin is intrinsically fluorescent. The results were captured using the Leica DC camera and Leica IM image management software. The appropriate filter was used to permit visualization of Doxorubicin's autofluorescence (excitation 488 nm, emission 550 nm; red fluorescence).

The results revealed that all the minicells fluoresced bright red suggesting that the Doxorubicin had been transferred into the minicell cytoplasm and, despite the extensive washing steps using the stirred cell ultrafiltration system, the Doxorubicin was unable to diffuse out of the minicell cytoplasm. This was surprising because, during the washing steps, the concentration gradient of Doxorubicin had been reversed, i.e., the Doxorubicin concentration in the minicell cytoplasm was higher than that of extracellular environment (BSG solution). Control minicells that were not incubated with the drug did not show any background autofluorescence.

To demonstrate that drug-packaging in minicells is not limited to doxorubicin, similar experiments were performed with another cancer chemotherapeutic drug, Vinblastine, that has low solubility in water. This drug does not autofluoresce; hence BODIPY-FL-conjugated Vinblastine (Molecular Probes, Eugene, Oreg., USA), a fluorescent analog, was used (excitation 505 nm, emission 513 nm; red fluorescence). The purified minicells were packaged with BODIPY-FL-conjugated Vinblastine as follows: the drug was initially dissolved in methanol (stock solution of 10 mg/ml) and diluted 1:10 in sterile PBS to give a stock solution of 1 mg/ml. 7×10$^9$ minicells in BSG solution were centrifuged, supernatant was discarded and the minicells were resuspended in 940 ul BSG and 60 ul of BODIPY-FL-conjugated Vinblastine solution (1 mg/ml stock solution). This gave a final concentration of 60 ug of drug in 1 ml of minicell suspension. The suspension was incubated overnight at 37° C. with rotation to allow the drug to diffuse into the minicell cytoplasm. The subsequent procedures of washing the excess drug by ultrafiltration up to the stage of final resuspension of drug-packaged minicells in BSG prior to visualization by fluorescence microscopy were the same as described above for Doxorubicin.

The drug-packaged minicells were mounted on glass slides and were visualized using a fluorescence microscope as above and the results were captured using the Leica DC camera and Leica IM image management software. The appropriate filter was used to permit visualization of red fluorescence of BODIPY-FL-conjugated Vinblastine.

The results revealed that all the minicells fluoresced bright red, indicating that the drug had been transferred into the minicell cytoplasm and, similarly to the observations for Doxorubicin, that the extensive washing steps, using the stirred cell ultrafiltration system, did not result in an efflux of the drug from the minicells into the extracellular fluid. This was surprising, too, because it is conventional wisdom thought that only highly hydrophilic solutes can enter into a bacterial cell via diffusion, possibly through porin channels found in bacterial membranes. The present results show, however, that even drugs that are not highly hydrophilic can diffuse through the membrane of a non-living bacterial cell derivative, such as a minicell. Control minicells that were not incubated with the drug did not show any background autofluorescence.

Example 2

Efficient Packaging of the Hydrophobic Cancer Chemotherapeutic Drug Paclitaxel in Bacterially Derived Intact Minicells This example shows that hydrophobic drugs can be packaged into the cytoplasm of bacterially derived intact minicells. Because the minicell surface membrane is composed of a phospholipid bilayer, diffusion of highly hydrophobic drugs across this barrier would not be expected.

Taxol (Paclitaxel; registered trademark of Bristol-Myers Squibb Company) is a tricyclic diterpene originally isolated from the bark of a Pacific yew tree, and more recently from the needles of the western yew tree *Taxus brevifolia*. Paclitaxel is one of the most important chemotherapeutic agents, having promising antitumor activity, especially against ovarian, breast, and lung cancers (Mekhail and Markman, 2002). Paclitaxel is an antimitotic agent that binds to tubulin in a 1:1 stoichiometry with tubulin heterodimers stabilizing microtubules and driving a high percentage of cells to arrest in the $G_2/M$ phase, progress slowly in the cell cycle without cytokinesis, form multinucleated polyploid cells, and undergo apoptosis. Paclitaxel has an extremely low aqueous solubility of 0.00025 mg/ml and has to be solubilized in certain cosolvents such as 50% Cremophore EL and 50% Ethanol.

To demonstrate that a hydrophobic drug like Paclitaxel could be transported into the minicell cytoplasm, a fluorescent derivative of Paclitaxel, Oregon Green® 488 conjugated Paclitaxel (Molecular Probes, Eugene, Oreg., USA; absorbance 496 nm, emission 524 nm) was used. Two different methods were adopted to solubilize the drug: (i) in ethanol (to give a 7.58 mM stock solution), and (ii) in ethanol:cremophore EL (1:1 vol/vol; 3.79 mM stock solution). Each stock solution was diluted 1:10 (vol/vol) in PBS to give 758 uM and 379 uM stock solutions, respectively. The latter stock solutions were added to the minicell suspension (10$^9$ minicells) at a 1:20 dilution to give a final concentration of Oregon Green® 488 conjugated Paclitaxel concentration in the minicell extracellular environment of 40 uM and 20 uM, respectively. The minicells were incubated with the drug at 37° C. overnight with rotation and subsequently washed with ultrafiltration as described in Example 1 for Doxorubicin and Vinblastine. The minicells were resuspended and visualised by fluorescence microscopy, also as described in Example 1.

The results revealed that all minicells fluoresced bright green, suggesting that both methods enabled the transfer of Paclitaxel from the extracellular milieu via the minicell membrane and into the cytoplasm of the minicell. This was surprising because it was not expected that the highly hydrophobic drug would diffuse into the minicell cytosol via the phospholipid bilayer (hydrophobic) membrane of the minicell. Additionally, similar to the observations in the experiments in Example 1, the reversal of the osmotic gradient during the extensive washing steps did not cause efflux of the drug out of the minicell cytoplasm.

The results in Examples 1 and 2 demonstrate that the simple techniques described above can be used to readily package both hydrophilic and hydrophobic drugs into minicell drug delivery vehicles.

Example 3

Methods for Determining the Drug Concentration in Bacterially Derived Intact Minicells This example demonstrates a method for determining the concentration of a drug in bacterially derived intact minicells.

More particularly, the example describes a method for determining the concentration of Doxorubicin present in minicells$_{DOX}$, and demonstrates the effect of Doxorubicin concentration in a loading solution. The application of drug-packaged minicells for therapeutic purposes requires the ability to characterize a packaged drug entity, including determining the quantity of packaged drug. Previously, however, there were no methods for effectively disrupting bacterially derived intact minicells or bacterial cells and extracting packaged drug molecules.

Abbreviations used below include (i) HCl; Hydrochloric acid (BDH AR MERCK, Australia), (ii) MeCN; Acetonitrile, Pesticide Residue grade (Burdick & Jackson, Michigan, USA), (iii) IPA; Isopropyl alcohol or 2-propanol, Pesticide Residue grade (Burdick & Jackson), MQ; MilliQ polished RO water (R≥$10^{18}$Ω), C18 & RP18; refer to the stationary phase packing chemistry present in the chromatography column (in this case it is an 18 carbon long hydrocarbon chain bonded to the silanol end group of the 5 micron (μm) diameter silica particles), (iv) HPLC & LC; High performance liquid chromatography, (v) MS; Mass spectrometry, (vi) MS/MS; Collision induced fragmentation of a selected parent ion to produce a defined daughter ion (useful in removing matrix effects and increasing signal/noise), (vii) ESI; Electrospray source ionisation (the ion current is generated in thermo-pneumatic spray at the head of the MS inlet).

$10^9$ intact minicells were separately incubated in a solution of Doxorubicin at final concentrations of 5, 10, 20, 30, 40, 50, 60, 80, 100, 120, 140, 160, 180, 200 and 250 μg/mL. The mixtures were incubated at 37° C. overnight with rotation. The minicells were harvested by centrifugation at 13,200 rpm/5 min and resuspended in sterile BSG. The minicell suspension was placed in an Amicon filtration chamber (0.2 μm pore size) and washed 10 times with 10 ml of BSG per wash. The minicells were collected and divided into duplicates of 5×$10^8$ minicells for Doxorubicin extraction.

The minicells were centrifuged at 13,200 rpm, and supernatant was discarded. To each pellet, 500 μL of 97 mM HCl-IPA was added, followed by 5 cycles of 1 minute vortexing and 1 minute sonication. MQ (500 μL) was added and the 5 cycles of 1 minute vortexing and 1 minute sonication were repeated. The extract was centrifuged for 5 mins at 13,200 rpm to pellet debris, and the supernatant was transferred to a HPLC 150 μL glass insert and vial. Because Doxorubicin autofluoresces, an HPLC fluorescence-based analysis of the extracted drug was developed and performed as follows. The HPLC method characteristics included (i) Mobile Phase: 100 mM ammonium formate+0.05% triethylamine (pH=3.5): MQ: MeCN was 28:42:30@1 mL/min, (ii) Stationary Phase: Merck Lichrosphere RP18, 5 μm, 4.0 mm×250 mm, (iii) Column Temperature: 40° C., (iv) Injection volume: 15 μL, (iv) Detection: Fluorescence—Excite 480 nm, Emission 550 nm, (v) HPLC system: A Shimadzu 10AVP system was used, comprising an autosampler, solvent degasser, quaternary pump, column heater (40° C.) and fluorescence detector, running version 7.2 SPI rev B software. Shimadzu Corporation (Kyoto Japan).

Doxorubicin measurements were done using both HPLC and LC-MS to confirm that the data were reliable. The LC-MS procedure and key characteristics included (i) Mobile Phase: 5 mM ammonium formate (pH=3.5): MeCN=76: 24@0.2 mL/min, (ii) Stationary Phase: Phenomenex Luna C18 (2), 5 μm, 2.0 mm×150 mm, (iii) Column Temperature: 30° C., (iv) Injection volume: 2 μL, (v) LC and MS system: Both the LC and MS systems were from Thermo-Finnigan (Boston, Mass., USA). The LC system comprised an autosampler with integrated column heater and pump. The column eluent was directly transferred to the electrospray ionization source of the Thermo-Finnigan LCQ-Deca ion trap mass spectrometer, (vi) Detection: The MS detector was operated in positive ion mode and MS/MS scan mode. The parent ion was set at m/z=543.9, yielding a daughter ion at m/z=396.8. The daughter ion was tracked for quantitation purposes.

The three fluorescent determinations and the MS results were plotted together (FIG. 1) to indicate their equivalent [DOX] determinations (within the error bars of the measurements). The results showed a clear correlation between the Doxorubicin concentration extracted from minicells$_{DOX}$ and the external loading concentration of Doxorubicin. These experiments were repeated 3 times with similar results. Additionally, the techniques were adapted to determine the concentration of other chemotherapeutic drugs like paclitaxel, Irinotecan, 5-Fluororacil and Cisplatin packaged in intact minicells.

Example 4

Drugs and the Attachment of Surface Ligands Do not Cause Minicell Instability or Loss of Membrane-Embedded Structures This example demonstrates that the packaging of drugs in minicells and attachment of ligands to the surface of drug-packaged minicells does not cause minicell instability, drug leakage or a loss of minicell membrane-embedded structures. The result is surprising because one would expect that drugs, particularly highly noxious chemotherapeutic drugs, in the cytoplasm would destabilize the minicell bilayer membrane.

A study was designed to determine if the packaging of drugs in minicells and/or the attachment of bispecific ligands to surface structures (e.g. O-antigen component of LPS) of minicells would cause drug leakage and/or loss of minicell bilayer-embedded structures with the bispecific ligand (e.g., LPS shedding). Minicells (5×$10^8$) were packaged with either Doxorubicin or Oregon Green® 488-conjugated Paclitaxel (Molecular Probes, Eugene, Oreg., USA) as described above. The drug concentration in the Minicells$_{DOX}$ and minicellspac was determined as described in Example 3, and the results showed 425 ng DOX and 245 ng Paclitaxel, respectively.

A BsAb with anti-S. Typhimurium O-antigen and anti-EGFR specificities was constructed as described in PCT/US2004/041010. Briefly, bispecific antibody (BsAb) was constructed by linking an anti-S. Typhimurium O-antigen monoclonal antibody (MAb) (IgG1; Biodesign) and a MAb directed against a target cell-surface receptor that is mouse anti-human EGFR (IgG2a; Oncogene) or mouse anti-human HER2/neu receptor (IgG1; Serotec). The two antibodies were cross-linked via their Fc regions using purified recombinant protein A/G (Pierce Biotechnology). Briefly, protein A/G (100 μg/ml final concentration) was added to 0.5 ml of a premixed solution containing 20 μg/ml each of anti-S. Typhimurium O-antigen and anti-human EGFR MAbs, and incubated overnight at 4° C. Excess antibodies were removed by incubation with protein G-conjugated magnetic beads and gentle mixing at room temperature for 40 min. After magnetic separation of the beads, the protein A/G-BsAb complex was incubated with 5×$10^8$ drug-packaged minicells for 1 hr at room temperature to coat them with antibody via binding of the O-antigen specific Fab arm to surface LPS. Alexa-Flour 488® (Molecular Probes; green fluorescence) or Alexa Fluor® 594 (Molecular Probes; red fluorescence) was used to conjugate to the BsAb. The minicells$_{DOX}$ were mixed with Alexa-Flour 488®-conjugated BsAb and minicells$_{Pac}$ were mixed with Alexa Fluor® 594-conjugated BsAb. The various minicell preparations were visualized using a Leica Fluorescence microscope using 100× objective and the appropriate filters for red and green fluorescence.

The results showed that BsAb attachment to the minicell$_{DOX}$ and minicell$_{Pac}$ surface was intense, appearing as a complete ring around the minicell cytoplasm. The individual drugs Doxorubicin and Paclitaxel also were visualized within the minicell cytoplasm. The drugs were extracted from the minicells as described above and the drug concentrations were determined. The drug concentrations were the same in minicell$_{DOX}$ and minicell$_{Pac}$, compared with $^{EGFR}$minicell$_{DOX}$ and $^{EGFR}$minicell$_{Pac}$ (i.e., 425 ng Doxorubicin and 245 ng Paclitaxel, respectively).

Similar results were obtained using other BsAbs, such a anti-Oantigen/anti-HER2/neu. This suggested that the methods are compatible with the development of a safe drug delivery vector, because the drug packaging and BsAb attachment did not result in instability of the vector or drug leakage from the intact minicell.

Example 5

Targeted Delivery In-Vitro of Doxorubicin to Non-Phagocytic Human Brain Cancer Cells via Ligand-Targeted and Doxorubicin-Packaged Minicells This example demonstrates that a chemotherapeutic drug, Doxorubicin, packaged in intact minicells carrying a cell surface-bound bispecific ligand, can (a) specifically bind to a target non-phagocytic mammalian cell surface, the EGF receptor on human brain cancer cells, and (b) deliver the drug intracellularly within the mammalian cell following endocytosis and breakdown of Doxorubicin-packaged minicells.

S. typhimurium minCDE-derived minicells were purified and packaged with Doxorubicin, as described in Example 1.

A bispecific antibody was constructed as described above and in U.S. patent application Ser. No. 10/602,021 and briefly described in example 4.

The anti-EGFR monoclonal antibody was selected because the target cells to be tested were human brain cancer cells U87-MG (ATCC, Rockville, Md., USA; human malignant astrocytoma epithelial cell line) that are known to overexpress the EGF receptor on the cell surface.

The bispecific antibody was tagged with a fluorescent dye to enable visualization and tracking, by fluorescence confocal microscopy, of the targeted minicells. The procedure was as follows. Alexa Fluor 488 protein labeling kit (Molecular Probes, Eugene, Oreg., USA) was used to label the bispecific antibody. Alexa Fluor 488 dye (absorbance 494 nm, emission 519 nm; green fluorescence) was conjugated via the free amine groups of the bispecific antibody according to the manufacturer's instructions.

U87-MG astrocytoma cells were grown on 15 mm coverslips in 12-well tissue culture plates (Cellstar; Greiner Bio-One GmbH, Frickenhausen, Germany). Cells were grown in RPMI 1640 medium with 5% cosmic calf serum (Hyclone, Logan, Utah, USA) and 2 mM glutamine and incubated at 37° C. with 5% $CO_2$. Cells were grown to 40% confluency and quadruple wells were treated as follows: (a) untreated cells as negative controls, (b) $10^8$ non-targeted empty minicells, (c) $10^8$ targeted empty minicells, (d) $10^8$ non-targeted Doxorubicin-packaged minicells, and (e) $10^8$ targeted Doxorubicin-packaged minicells. The incubation reaction was terminated after 8 hrs in 2 wells of each sample and the remaining duplicate samples were terminated after 24 hrs. After incubation, the cells were washed four times with PBS and fixed with 4% formaldehyde for 10 min. The fixative was washed three times with PBS and the coverslips were inverted onto glass microscope slides with glycerol. The coverslips were sealed with 1% agarose.

The slides were viewed by fluorescence confocal microscopy (Fluoview, Olympus America, Melville, N.Y., USA). Fluorescence and Differential Image Contrast (DIC) images were collected and the results revealed that within 8 hrs of incubation, targeted (carrying the Alexa Fluor 488-conjugated bispecific antibody; green fluorescence) Doxorubicin-packaged minicells showed most cells covered by several green fluorescent dots, while the non-targeted (lacking the fluorescence-labeled bispecific antibody) showed only some green fluorescent dots on very few cells. This suggested that the bispecific antibody specifically enabled the Doxorubicin-packaged minicells to strongly adhere to the surface of the astrocytoma cells, presumably via the EGF receptor. After 24 hrs co-incubation of astrocytoma cells and Doxorubicin-packaged minicells (targeted and non-targeted), the results, when visualized for red fluorescence (Doxorubicin autofluorescence is red), showed that most astrocytoma cells carried intense red fluorescent dots on the cell surface and many cells showed diffuse red fluorescence within the cell cytoplasm, as determined by viewing sections through the cell by fluorescence confocal microscopy. This result contrasted with that for astrocytoma cells incubated for 24 hrs with non-targeted Doxorubicin-packaged minicells, where only a few red fluorescent dots (non-specific adhesion of minicells) could be observed on a few cells. This suggests that many of the Doxorubicin-packaged minicells had been internalized, most likely via EGF receptor-mediated endocytosis and that some minicells had broken down and released the Doxorubicin within the astrocytoma cell cytoplasm. The results were further confirmed when the green fluorescent and red fluorescent images were merged to reveal that most of the green dots co-localized with the red dots, resulting in yellow dots. The diffuse red fluorescence observed earlier within the astrocytoma cell cytoplasm remained red, suggesting that the Doxorubicin (red autofluorescence) was no longer packaged within the minicells (revealed green by minicell surface localized bispecific antibody), further suggesting that some minicells that had been endocytosed had broken down and released the Doxorubicin within the astrocytoma cell cytoplasm.

Example 6

Efficiency of Minicell-Mediated Drug Delivery to Non-Phagocytic Mammalian Cells

This example demonstrates the efficiency of minicell-mediated drug delivery to non-phagocytic mammalian cells. A colorimetric cytotoxicity assay (Promega; CellTiter 96 Aqueous One™ was used. MDA-MB-468 human breast adenocarcinoma cells were treated with $^{EGFR}$minicells$_{DOX}$ or controls comprising free Doxorubicin and $^{non-targeted}$Minicells$_{DOX}$. MDA-MB 468 cells were seeded at $5 \times 10^6$ cells in T75 flasks and incubated for 48 hrs to obtain $\sim 1 \times 10^7$ cells/flask. The media was changed and cells were treated with $10^9$ $^{non-targeted}$minicells$_{DOX}$ or $^{EGFR}$Minicells$_{DOX}$. Free Doxorubicin (50 ng/ml) was also included as a positive control. The cells were incubated for 24 hrs, washed thoroughly with 3 changes of PBS and trypsinized. Viable cells were counted in a haemocytometer using the trypan blue exclusion method. $1 \times 10^4$ cells/ml per well were aliquoted into 24-well plates (6 wells per treatment) and incubated for 3, 4, 5, and 6 days with media changes everyday. MTS assay was performed at each time point according to the manufacturers instructions. Briefly, 100 µL of MTS reagent was added to each well and color development was monitored over 2.5 hrs to 4 hrs. 100 µL from each well was transferred to a 96-well plate and the absorbance was read at 490 nm.

Figure 2:
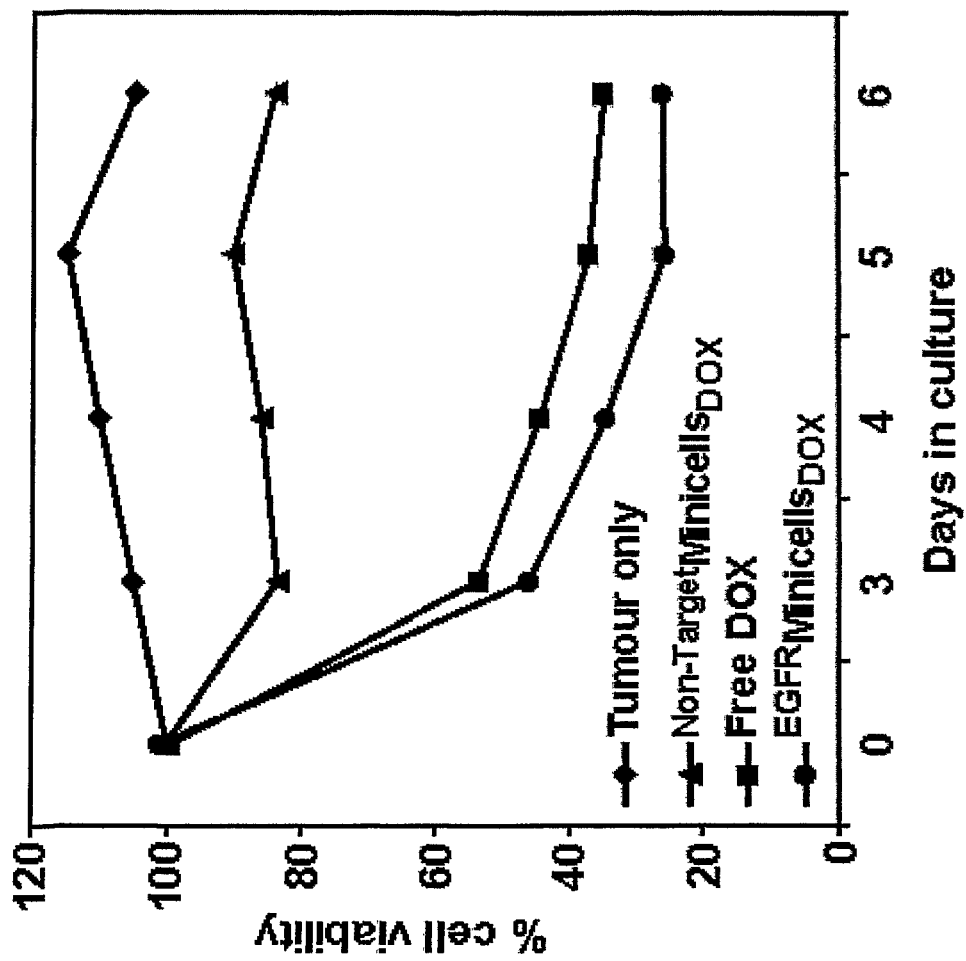
FIG. 2 is a chart showing drug delivery via minicells$_{DOX}$ to human breast adenocarcinoma cells (MDA-MB-468) in-vitro. A cell cytotoxicity assay was performed on cells treated with EGFR-targeted minicells$_{DOX}$ ($^{EGFR}$minicells$_{DOX}$), non-targeted minicells$_{DOX}$ ($^{non-targeted}$minicells$_{DOX}$), free Doxorubicin and untreated cells. Within 6 days after treatment, cells treated with either free Doxorubicin or $^{EGFR}$minicells$_{DOX}$ exhibited only about 30% viability. Untreated cells and cells treated with $^{non-targeted}$minicells$_{DOX}$ showed normal cell viability.

The results showed (FIG. 2) that the cytotoxicity of $^{EGFR}$Minicells$_{DOX}$ was similar to that of free Doxorubicin, suggesting that $^{EGFR}$Minicells$_{DOX}$ delivered Doxorubicin in its active form to the MDA cells and that the efficiency of drug delivery was over 95%. $^{non-targeted}$Minicells$_{DOX}$ did not show any toxicity to the cancer cells, suggesting that the targeting mechanism was important for safety of the minicell-based drug therapy, because non-phagocytic mammalian cells do not appear to non-specifically endocytose the minicells.

Example 7

Highly Efficient Delivery of Chemotherapeutic Drug Doxorubicin Via Targeted and Drug-Packaged Minicells to Human Breast Cancer Xenografts in Nude Mice This example demonstrates that bispecific ligand-targeted and Doxorubicin-packaged intact minicells can effect regression of human breast cancer cell tumor xenografts established in 6 week old female athymic nude mice.

As described above, minicells were obtained from an *S. typhimurium* minCDE-mutant strain and were purified using a gradient centrifugation/filamentation/filtration/endotoxin removal procedure. The purified minicells were packaged with chemotherapeutic drug Doxorubicin as described in Example 1.

A bispecific antibody was constructed as described in Example 3. An anti-EGFR monoclonal antibody was selected because the xenografted cells were human breast cancer cells MDA-MB-468 that are known to overexpress the EGF receptor on the cell surface.

Recombinant minicells ($10^{10}$) were incubated with the protein A/G-bispecific antibody for 1 hour at room temperature, to coat the minicells with the antibody via its anti-LPS Fab region.

The mice used in this example were purchased from Animal Resources Centre, Perth, WA, Australia, and all animal experiments were performed in compliance with the guide of care and use of laboratory animals and with Animal Ethics Committee approval. The experiments were performed in the NSW Agriculture accredited small animal facility at EnGeneIC Pty Ltd (Sydney, NSW, Australia). Human breast adenocarcinoma cells (MDA-MB-468, ATCC; human mammary epithelial cells; non-phagocytic) were grown in tissue culture to full confluency in T-75 flasks in RPMI 1640 medium supplemented with 5% Bovine Calf Serum (GIBCO-BRL Life Technologies, Invitrogen Corporation, Carlsbad, Calif., USA) and glutamine (Invitrogen) in a humidified atmosphere of 95% air and 5% $CO_2$ at 37° C. $1 \times 10^6$ cells in 50 uL serum-free media together with 50 uL growth factor reduced matrigel (BD Biosciences, Franklin Lakes, N.J., USA) were injected subcutaneously between the shoulder blades of each mouse using a 23-gauge needle. The tumors were measured twice a week using an electronic digital caliper (Mitutoyo, Japan, precision to 0.001) and mean tumor volume was calculated using the formula, length (mm)×width$^2$ (mm)× 0.5=volume (mm$^3$). 16 days post-implantation, the tumors reached volumes between 50 mm$^3$ and 80 mm$^3$, and mice were randomized to seven different groups of 11 per group.

The experiment was designed as follows. Group 1 (control) received no treatment. Group 2 (control) received free Doxorubicin (5 µg/gm of mouse body weight) intratumorally. This control was included to determine the effect of free Doxorubicin on tumor cells and to assess toxic side-effects. Group 3 (control) was the same as group 2, except that the Doxorubicin was administered intravenously. Group 4 (control) received the anti-O antigen/anti-EGFR BsAb and free Doxorubicin intravenously to show the effect of BsAb in the absence of minicells. Groups 5 and 6 received $^{non-targeted}$minicells$_{DOX}$ intravenously and intratumorally, respectively, to determine if drug-packaged but non-targeted minicells could effect tumor stabilization. Groups 7 and 8 received EGFR-targeted $^{EGFR}$Minicells$_{DOX}$ intravenously and intratumorally, respectively, to determine if receptor-targeted, drug-packaged minicells could effect tumor stabilization. Group 8 was included to determine if the targeted, Doxorubicin-packaged minicells given in the tail vein could follow the required sequence of events to achieve tumor stabilization and/or regression: i.e., permeate the leaky vasculature at the tumor site (shoulder blade region), diffuse through the tumor microenvironment, specifically bind to the human breast cancer cells, be endocytosed, broken down intracellularly and release the drug payload in its bioactive form into the cancer cell cytoplasm to result in cell death and hence either tumor stabilization and/or regression. Minicells were administered at a dose of $10^8$ and all treatments were given on days 17, 24, 27 and 56 post-xenograft establishment. All measurements were performed by an investigator who was blinded to the treatments administered. Statistical analysis was performed by analysis of variance (ANOVA) and P<0.05 was considered to be statistically significant.

The results showed (FIG. 3) that highly significant (p=0.0004) tumor stabilization/regression was only observed with $^{EGFR}$Minicells$_{DOX}$ treatment, whether given intravenously or intratumorally. No tumor regression was observed with $^{non-targeted}$minicells$_{DOX}$, suggesting that the BsAb-mediated targeting was essential. At day 63, the treatment for the minicells$_{DOX}$ group was changed to $^{EGFR}$Minicells$_{DOX}$ treatment to determine if the large tumor volumes (800 mm$^3$ to 1,200 mm$^3$) could be regressed via the targeted therapy. The result was a dramatic tumor regression; by day 79, with just two $^{EGFR}$Minicells$_{DOX}$ treatments, the tumor volumes had regressed to between 100 mm$^3$ and 150 mm$^3$. The complete experiment was performed 3 times, each time yielding similar results. This showed that the BsAb-targeted minicells could specifically deliver a chemotherapeutic drug to a human tumor xenograft in-vivo.

The result is a first demonstration of targeted in-vivo drug delivery to non-phagocytic mammalian cells mediated by bacterially derived intact drug-packaged minicells.

Interestingly, the free Doxorubicin given in the tail vein of mice (Groups 3 and 4) showed severe reaction at the site of the injection, a well known side-effect of free Doxorubicin intravenous injections in humans. This reaction, known as Phlebitis, is thought to be caused by drug extravasation at the site of injection, and associated killing of normal cells in the localized region. In contrast, the mice given targeted or non-targeted Doxorubicin-packaged minicells did not show any adverse reaction at the site on the injection, suggesting that the minicell-packaged Doxorubicin prevented free Doxorubicin reactivity with skin tissue at the site of injection. Additionally, unlike liposomal delivery vectors, e.g., DOXIL (liposomal doxorubicin), the drug did not leak from minicells.

Figure 3:
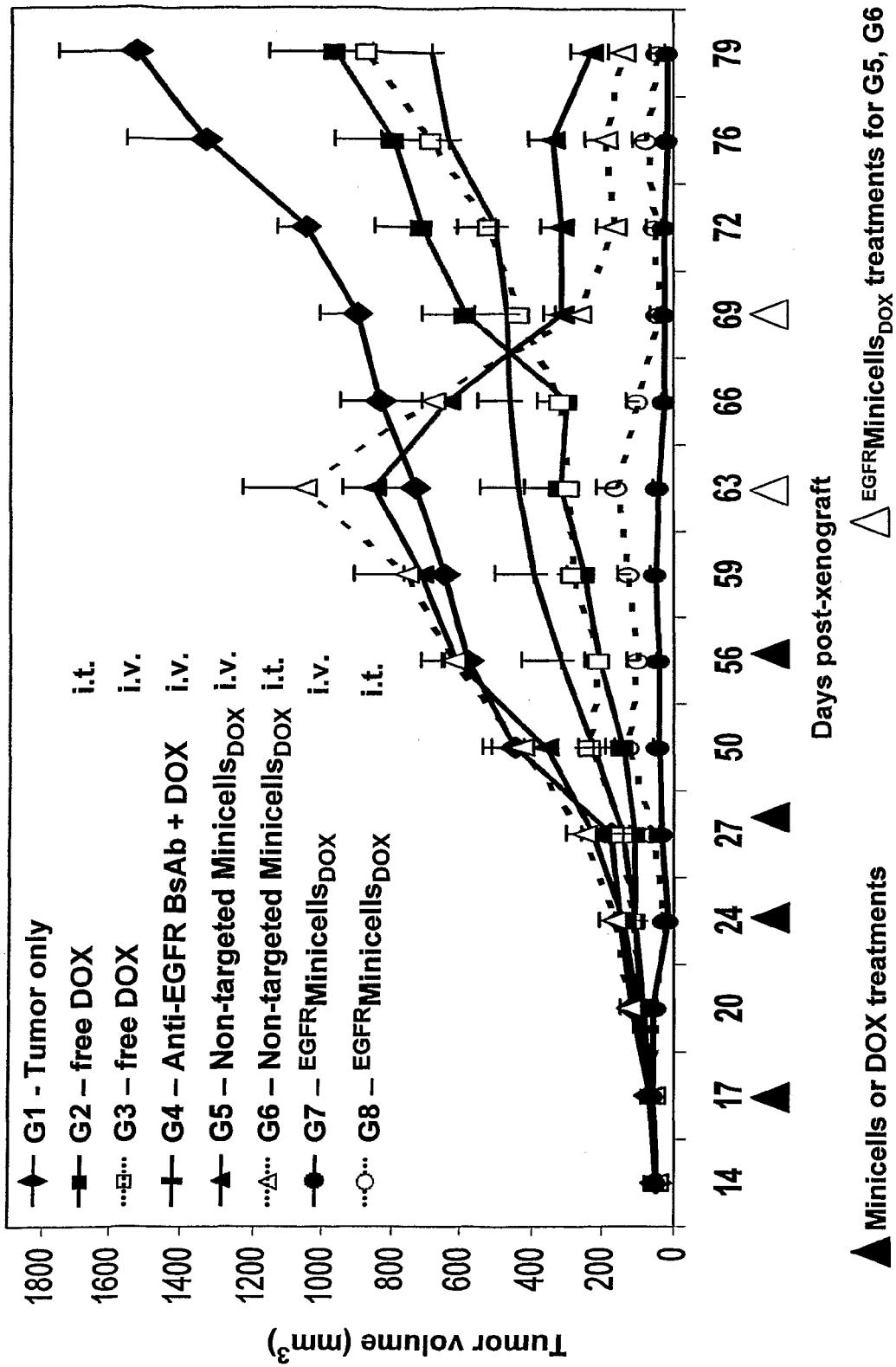
FIG. 3 is a chart showing a highly significant therapeutic effect of EGFR-targeted, Doxorubicin-packaged minicells ($^{EGFR}$minicells$_{DOX}$) on human breast cancer xenografts. Tumor volume is shown on the y-axis, and days post-xenograft establishment are shown on the x-axis. Solid triangles below the x-axis indicate the days on which various treatments were administered. Open triangles below the x-axis indicate a change in the treatment of control groups G5 and G6, where $^{EGFR}$minicells$_{DOX}$ were administered instead of $^{non-targeted}$minicells$_{DOX}$. The legend identifies the various treatments administered to each of 8 groups of mice (n=11 per group).

These results suggest the following: (a) minicells are able to package a potentially highly toxic drug like Doxorubicin in the minicell cytoplasm and the drug does not appear to leak out of the minicell membrane. Hence, the lack of skin reactivity to at the site of the tail vein injection (Groups 5 and 7)

that was seen with free Doxorubicin (Groups 3 and 4), (b) Doxorubicin-packaged minicells are safe to at least the nude mice when the minicells are injected intravenously or intratumoraly (Groups 5 to 8), suggesting that the free endotoxin (lipopolysaccharide) removal procedure adopted and previously invented by the current inventors (U.S. patent application No. PCT/IB02/04632) is sufficient to provide a dose of minicells sufficiently free of endotoxin to be safe for intravenous or intratumoral subcutaneous administration, (c) targeted minicells appear to be small enough to permeate the leaky tumor neovasculature, to enable Doxorubicin-packaged minicells to enter into the tumor microenvironment, (d) targeted Doxorubicin-packaged minicells appear to specifically bind to the EGF receptor that is known to be overexpressed on the surface of MDA-MB-468 cells and post-endocytosis, the minicells break down and release Doxorubicin, resulting in tumor cell death and the observed tumor regression (Group 7; FIG. 3), (e) following intravenous injection the targeted and Doxorubicin-packaged minicells reach the tumor microenvironment in significant concentration to achieve tumor regression. Accordingly, minicells do not appear to have been eliminated by circulating professional phagocytic cells in significant quantities to obviate the observed therapeutic effect.

Example 8

Highly Efficient Delivery of Hydrophobic Chemotherapeutic Drug Paclitaxel Via Targeted and Drug-Packaged Minicells to Human Breast Cancer Xenografts in Nude Mice This example demonstrates highly efficient delivery of a hydrophobic chemotherapeutic drug, Paclitaxel, to human breast cancer xenografts in nude mice via targeted and drug-packaged minicells. The experiment shown in example 7 was repeated using $^{EGFR}$Minicells$_{Paclitaxel}$ as the experimental treatment. The treatments included, (i) G1—tumor only, (ii) G2—free Paclitaxel (400 µg) given intratumorally, (iii) G3—Free Paclitaxel (400 µg) given intravenously, (iv) G4—anti-O antigen/anti-EGFR BsAb and free Paclitaxel (400 µg) given intravenously, (v) G5—$^{non-targeted}$minicells$_{Pac}$ given intravenously, (vi) G6—$^{non-targeted}$minicells$_{Pac}$ given intratumorally, (vii) G7—$^{EGFR}$minicells$_{Pac}$ given intravenously, (viii) G8—$^{EGFR}$minicells$_{Pac}$ given intratumorally. The various treatments were given on days 15, 21, 26, 29 and 33. $1 \times 10^8$ minicells were used in each minicell treatment.

Figure 4:
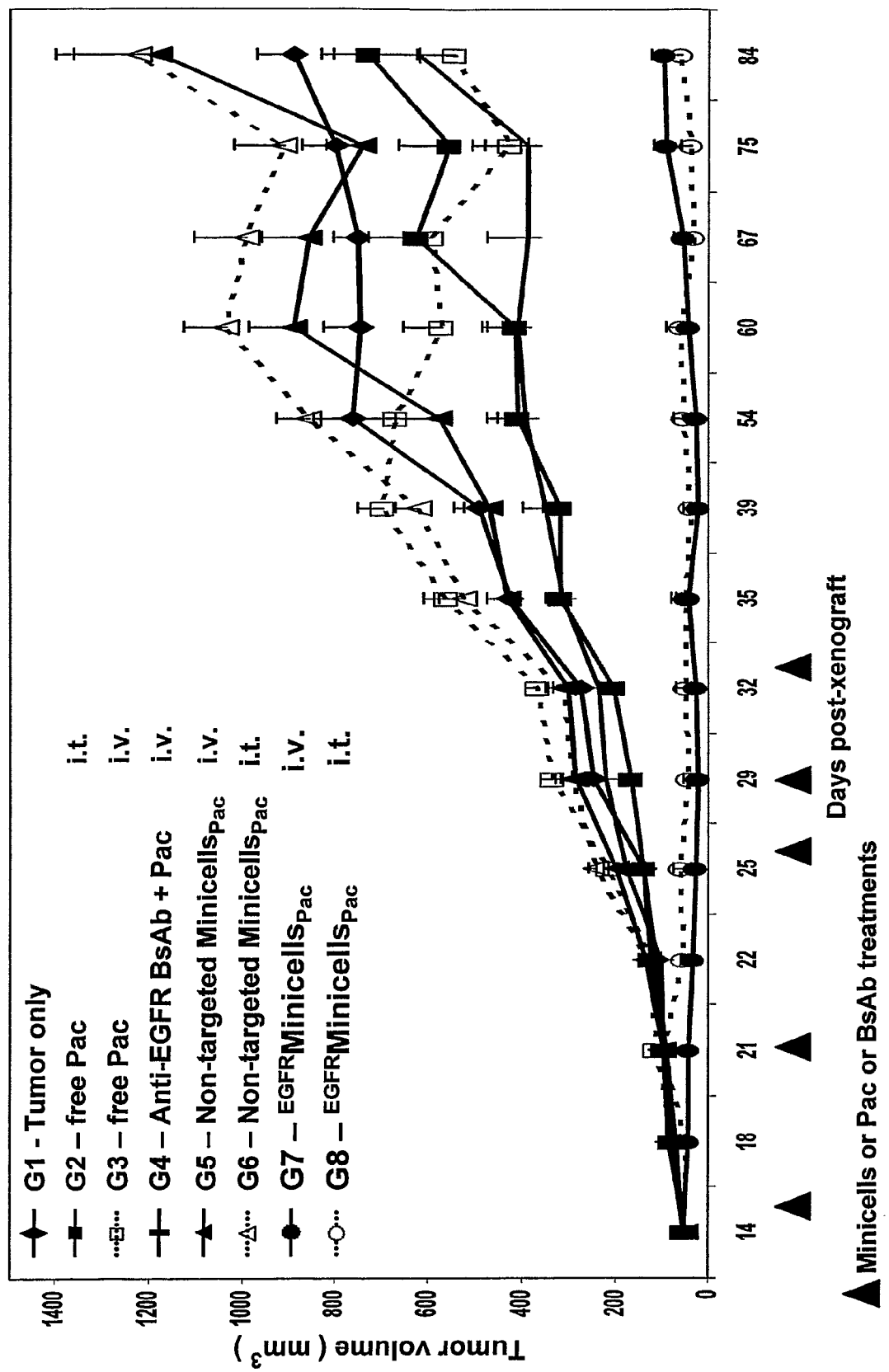
FIG. 4 is a chart showing a highly significant therapeutic effect of EGFR-targeted, Paclitaxel-packaged minicells ($^{EGFR}$minicells$_{Pac}$) on human breast cancer xenografts. Tumor volume is shown on the y-axis, and days post-xenograft establishment are shown on the x-axis. Solid triangles below the x-axis indicate the days on which various treatments were administered. The legend identifies the various treatments administered to each of 8 groups of mice (n=11 per group).

The results showed (FIG. 4) highly significant (p=0.0004) tumor stabilization/regression in mice treated with $^{EGFR}$minicells$_{Pac}$ and, once more, it did not matter whether the treatment was given intravenously or intratumorally. The control treatments including $^{non-targeted}$minicells$_{Pac}$, BsAb and free paclitaxel had a negligible effect on tumor growth. Throughout the experiment, mice did not show any overt signs of toxicity such as fever, lethargy, loss of appetite or death. The experiment was repeated 3 times with similar results.

This result is particularly significant, because other drug delivery vectors, like liposomes, nanoparticles, etc., have not successfully packaged therapeutically significant amounts of highly hydrophobic drugs like Paclitaxel. In most cases, attempts were made to change the chemical structure of the vector or the drug to enable drug packaging, often resulting in loss of bioactivity. Our result is the first showing that not only can such drugs be readily packaged in intact minicells, but they can be safely delivered specifically to target diseased cells in-vivo to achieve a therapeutic effect.

Example 9

Demonstration of Versatility of Targeted Minicell-Based Drug Delivery to Mammalian Cells This example demonstrates the following: (i) targeted, drug-packaged minicell vectors are versatile enough to achieve a therapeutic effect in a range of different non-phagocytic cells, (ii) the targeting mechanism is versatile enough to enable the use of different cell-surface receptor targets on diseased cells and is not restricted to the EGF receptor, and (iii) the minicell vector itself is versatile enough to enable the use of minicells derived from different bacterial genera.

In a single nude mouse xenograft experiment, (i) human ovarian cancer cells (SKOV3; ATCC. USA) were used to establish the tumor xenograft, (ii) the targeting BsAb was constructed using anti-O antigen MAb and anti-HER2/neu MAb (The latter receptor is known to be overexpressed on the surface of SKOV3 cells.), and (iii) minicells used for the treatment were derived both from *S. Typhimurium* and *E. coli* minCDE-strains. The minicells were packaged with Doxorubicin. $^{non-targeted}$minicells$_{DOX}$, BsAb (anti-HER2/anti-O antigen) and free Doxorubicin were included as controls.

Figure 5:
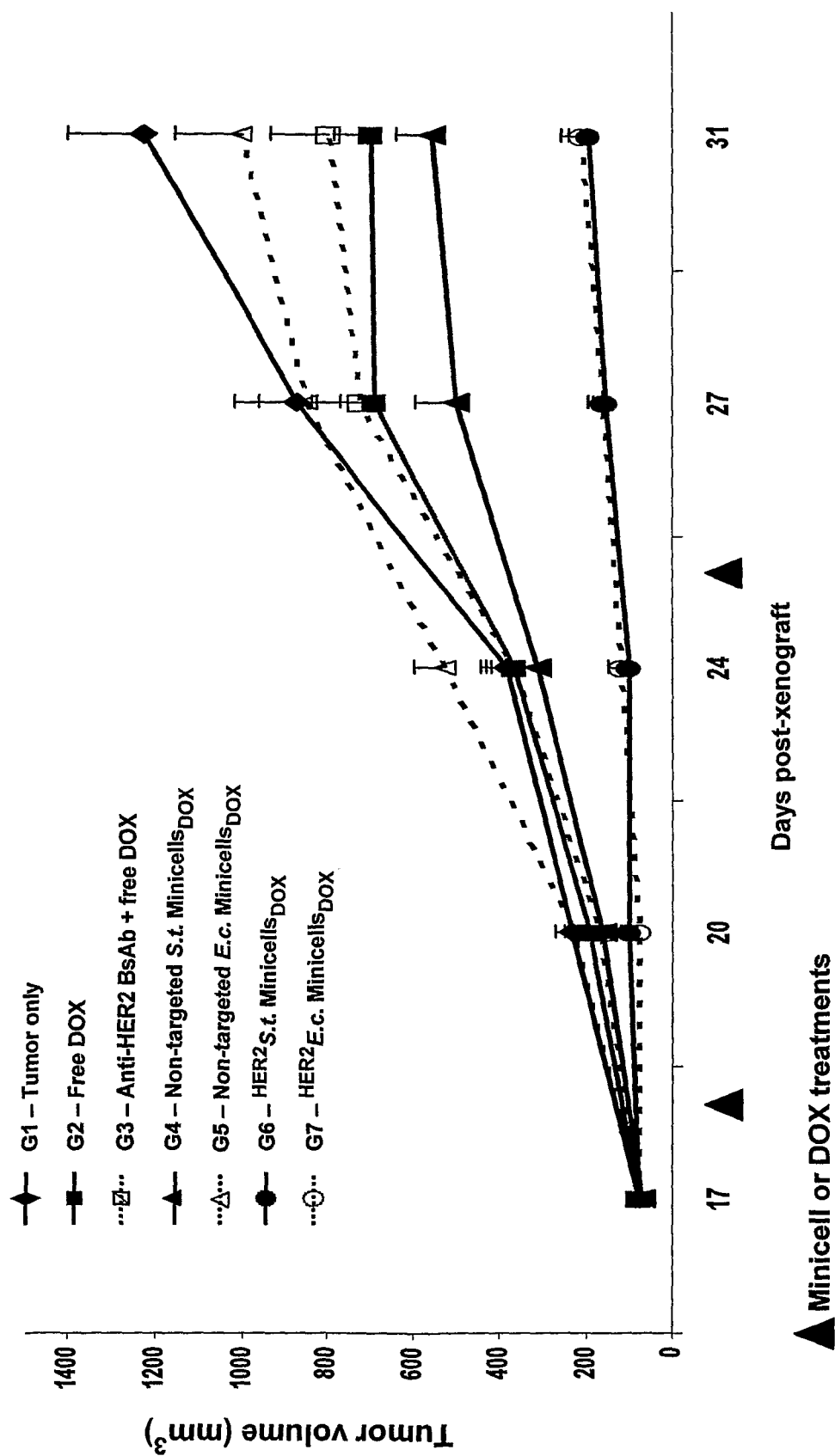
FIG. 5 is a chart showing a highly significant therapeutic effect of HER2/neu-targeted, Doxorubicin-packaged minicells ($^{HER2}$minicells$_{DOX}$) on human ovarian cancer xenografts. The minicells were derived from S. Typhimurium (S.t.) or E. Coli (E.c.) minCDE-parent strains. Tumor volume is shown on the y-axis, and days post-xenograft establishment are shown on the x-axis. Solid triangles below the x-axis indicate the days on which various treatments were administered. The legend identifies the various treatments administered to each of 7 groups of mice (n=11 per group).

The results showed (FIG. 5) significant tumor stabilization in mice treated with either *S. Typhimurium* minCDE- or *E. coli* minCDE-derived $^{HER2}$minicells$_{DOX}$ (p=0.004). The SKOV3 xenografts grew much more rapidly than MDA-MB-468 xenografts, and the experiment could only be followed up to 31 days post-xenograft establishment because the control animals had reached the point of death or euthanasia.

These results demonstrated (i) that intact minicells can be used to deliver drugs in-vivo to a range of different non-phagocytic mammalian cells, (ii) that intact minicell vectors can be targeted to a diverse range of cell surface receptors found on the diseased cells, and (iii) that minicells can be derived from different bacterial genera or species, yet function in a similar way, particularly with respect to drug delivery to target cells in-vivo.

Example 10

The Relationship Between Targeted, Drug-Packaged Minicell Dose and Therapeutic Effect on Human Tumor Xenografts in Nude Mice This example demonstrates the dose-effect relationship for drug-packaged minicells. More specifically, the example shows the dose of targeted, drug-packaged minicells required to achieve maximal therapeutic effect on human tumor xenografts in nude mice.

MDA-MB-468 (human breast adenocarcinoma) cells were established as xenografts between the shoulder blades of Balb/c nu/nu mice. *S. Typhimurium* minCDE-derived minicells were packaged with Doxorubicin using two different external Doxorubicin concentrations, 60 µg/ml and 200 µg/ml as described in example 3. The minicells$_{DOX}$ were purified (example 1) and samples were analyzed by HPLC to determine the concentration of Doxorubicin packaged within $10^8$ minicells. The results showed that at external Doxorubicin concentrations of 60 µg/ml and 200 µg/ml, $10^8$ minicells packaged 85 ng and 660 ng of Doxorubicin, respectively.

The minicells$_{DOX}$ were then targeted to the EGFR that is overexpressed on MDA-MB-468 cells and six different mouse intravenous doses were prepared, (i) G1-$10^8$ $^{EGFR}$minicells$_{DOX}$ carrying a total of 660 ng Doxorubicin, (ii) G2-$10^8$ $^{EGFR}$minicells$_{DOX}$ carrying a total of 85 ng Doxorubicin, (iii) G3-$10^7$ $^{EGFR}$minicells$_{DOX}$ carrying a total of 66 ng Doxorubicin, (iv) G4-$10^7$ $^{EGFR}$minicells$_{DOX}$ carrying a total of 8.5 ng Doxorubicin, (v) G5-$10^6$ $^{EGFR}$minicells$_{DOX}$ carrying a total of 6.6 ng Doxorubicin, and (vi) G6-$10^6$ $^{EGFR}$minicells$_{DOX}$ carrying a total of 0.85 ng Doxorubicin. Post-xenograft establishment with tumor volumes between 50 mm to 80 mm, the various doses were intravenously administered to the mice. Tumor volumes were measured as previously described.

Figure 6:
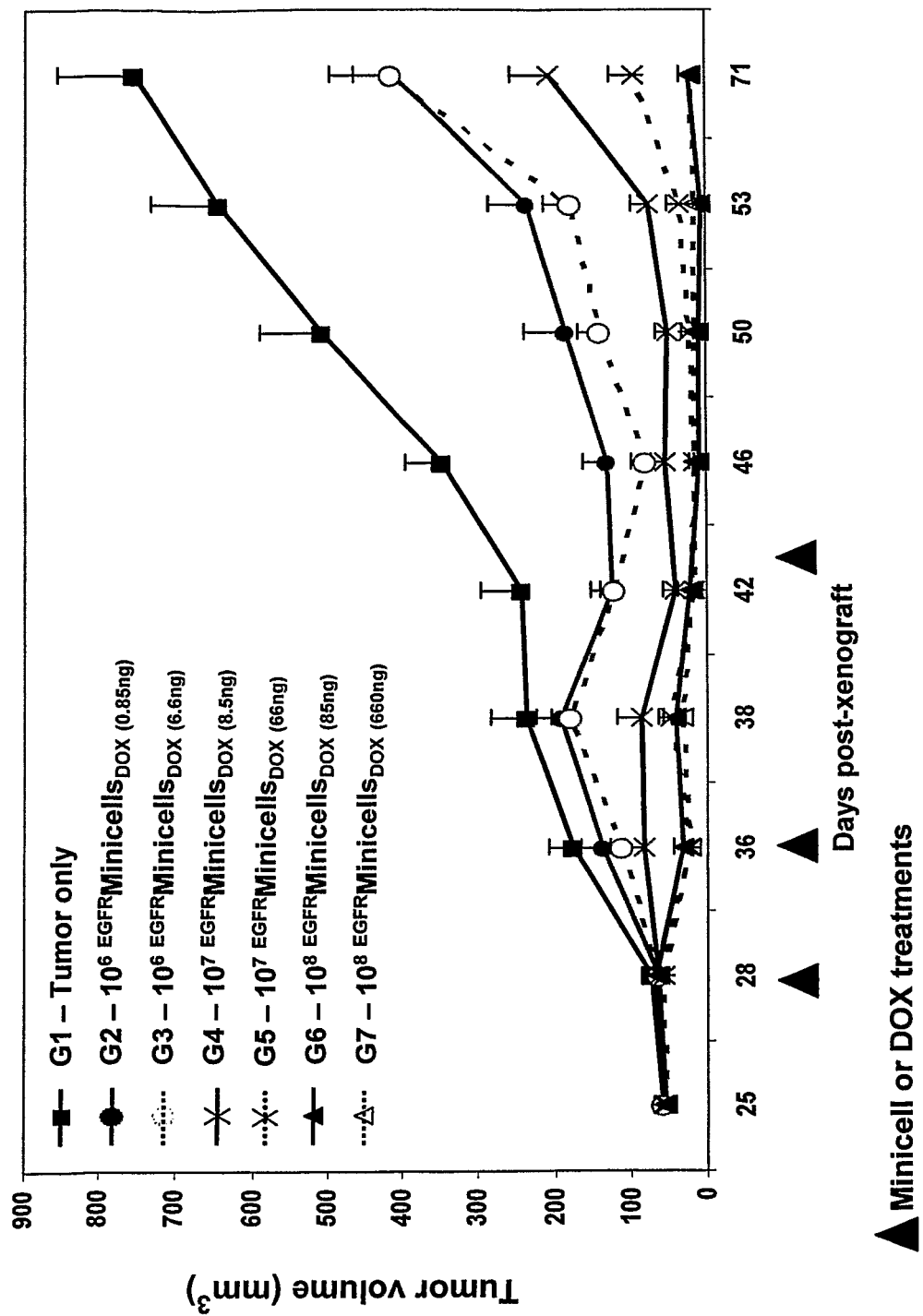
FIG. 6 is a chart showing a dose-response effect on tumor stabilization/regression by EGFR-targeted, Doxorubicin-packaged minicells ($^{EGFR}$minicells$_{DOX}$). MDA-MB-468 tumor xenografts were established in Balb/c nu/nu mice, and groups (n=11) were treated intravenously with 10$^6$, 10$^7$ or 10$^8$ $^{EGFR}$minicells$_{DOX}$ containing two different concentrations of Doxorubicin. Tumor volume is shown on the y-axis, and days post-xenograft establishment are shown on the x-axis. Solid triangles below the x-axis indicate the days on which various treatments were administered. The legend identifies the various treatments administered to each of 7 groups of mice.

The results showed (FIG. 6) a clear relationship between minicell dose and the therapeutic effect. In terms of tumor stabilization/regression, $10^8$ $^{EGFR}$minicells$_{DOX}$ were more effective than $10^7$ $^{EGFR}$minicells$_{DOX}$, which in turn were more effective than $10^6$ $^{EGFR}$minicells$_{DOX}$. Interestingly, there was no major difference in the Doxorubicin concentration between minicells administered to groups 3 and 4 (6.6 ng and 8.5 ng respectively) and groups 5 and 6 (66 ng and 85 ng). However, the treatment in G4 was more effective than G3 and, similarly, treatment in G6 was more effective than G5. This suggested that within the range of minicell and drug concentrations analyzed in this experiment, the therapeutic effect correlated to minicell numbers rather than to the concentration of drug carried within the minicells.

CITED PUBLICATIONS

This application incorporates by reference each of the following publications:

Alberts et al., Intraperitoneal cisplatin plus intravenous cyclophosphamide versus intravenous cisplatin plus intravenous cyclophosphamide for Stage III ovarian cancer, *N. Engl. J. Med.*, 335: 1950-1955 (1996).

Allen et al., Chronic liposome administration in mice: effects on reticuloendothelial function and tissue distribution, *J. Pharmacol. Exp. Therap.*, 229: 267-275 (1984).

Allen T M, Liposomes: opportunities in drug delivery, *Drugs*, 54 Suppl 4: 8-14 (1997).

Alkan-Onyuksel et al., A mixed micellar formulation suitable for the parenteral administration of taxol, *Pharm. Res.*, 11(2): 206-12 (1994).

Arndt et al., Alkylphospholipid liposomes: preparation, properties and use in cancer research, *Drugs of Today*, 34 (Suppl. F): 83-96 (1998).

Barenholz, Liposome application: problems and prospects, *Curr. Opin. Colloid Interface. Sci.*, 6: 66-77 (2001).

Batra et al., Receptor-mediated gene delivery employing lectin-binding specificity, *Gene Ther.*, 1(4): 255-60 (1994).

Becker et al., Gene therapy of prostate cancer with the soluble vascular endothelial growth factor receptor Flk1, *Cancer Biol. Ther.*, 1(5):548-53 (2002).

Borges-Walmsley & Walmsley, The structure and function of drug pumps, *Trends Microbiol.* 9: 71-79 (2001).

Britton et al., "Characterization of a prokaryotic SMC protein involved in chromosome partitioning," *Genes Dev.*, 12: 1254 (1998).

Carter, Improving the efficacy of antibody-based cancer therapies, *Nat. Rev. Cancer,* 1(2): 118-29 (2001).

Chan et al., Prospective randomized trial of docetaxel versus Doxorubicin in patients with metastatic breast cancer, *J. Clin. Oncol.*, 17:2341-54 (1999).

Chonn & Cullis, Recent advances in liposomal drug-delivery systems, *Curr. opinion in Biotechnology*, 6(6): 698-708 (1995).

Cowan et al., Randomized trial of Doxorubicin, bisantrene, and mitoxantrone in advanced breast cancer, *J. Natl. Cancer Inst.*, 83: 1077-84 (1991).

Cullis et al., Influence of pH gradients on the transbilayer transport of drugs, lipids, peptides and metal ions into large unilamellar vesicles, *Biochim. Biophys. Acta*, 1331: 187-211 (1997).

Daemen et al., Liposomal Doxorubicin-induced toxicity: depletion and impairment of phagocytic activity of liver macrophages, *Int. J Cancer*, 61: 716-721 (1995).

Daemen et al., Toxicity of Doxorubicin entrapped within long-circulating liposomes, *J. Controlled Release*, 44: 1-9 (1997).

de Haard et al., A large non-immunized human Fab fragment phage library that permits rapid isolation and kinetic analysis of high affinity antibodies, *J. Biol. Chem.*, 274:18218-18230 (1999).

DeMario M D and Ratain M I. Oral chemotherapy: rationale and future directions, *J. Clin. Oncol.*, 16(7): 2557-2567 (1998).

Dubel et al., Bifunctional and multimeric complexes of streptavidin fused to single chain antibodies (scFv), *J. Immunol. Methods*, 178: 201-209 (1995).

Gabizon et al., Pharmacokinetics of pegylated liposomal Doxorubicin: review of animal and human studies, *Clin. Pharmacokinet.*, 42: 419-36 (2003).

Glennie et al., Preparation and performance of bispecific F(ab' gamma)2 antibody containing thioether-linked Fab' gamma fragments, *J. Immunol.*, 139(7): 2367-75 (1987).

Gosselin & Lee, Folate receptor-targeted liposomes as vectors for therapeutic agents, *Biotechnol. Annu. Rev.*, 8: 103-31 (2002).

Gregoriadis, Targeting of drugs: implications in medicine, *Lancet, II:* 241-6 (1981).

Griffiths et al., Isolation of high affinity human antibodies directly from large synthetic repertoires, *EMBO J.*, 13: 3245-3260 (1994).

Harry, "Bacterial cell division: Regulating Z-ring formation," *Mol. Microbiol.*, 40: 795 (2001).

Heim et al., "Wavelength mutations and posttranslational autoxidation of green fluorescent protein," *Proc. Natl. Acad. Sci. USA*, 91: 12501 (1994).

Henderson et al., Randomized clinical trial comparing mitoxantrone with Doxorubicin in previously treated patients with metastatic breast cancer, *J. Clin. Oncol.*, 7: 560-71 (1989).

Hiraga et al., "Chromosome partitioning in *Escherichia coli*: novel mutants producing anucleate cells," *J. Bacteriol.*, 171: 1496 (1989).

Hoshida et al., Gene therapy for pancreatic cancer using an adenovirus vector encoding soluble flt-1 vascular endothelial growth factor receptor, *Pancreas*, 25(2): 111-21 (2002).

Hu et al., Minibody: A novel engineered anti-carcinoembryonic antigen antibody fragment (single-chain Fv-CH3) which exhibits rapid, high-level targeting of xenografts, *Cancer Res.*, 56: 3055-3061 (1996).

Hu & Lutkenhaus, "Topological regulation of cell division in *Escherichia coli* involves rapid pole to pole oscillation of the division inhibitor MinC under the control of MinD and MinE," *Mol. Microbiol.*, 34: 82 (1999).

Hudson & Souriau, Recombinant antibodies for cancer diagnosis and therapy, *Expert Opin. Biol. Ther.*, 1: 845-855 (2001).

Hudson & Souriau, Engineered antibodies, *Nat. Med.*, 9(1): 129-34 (2003).

Hung et al., Development of clinical trial of E1A gene therapy targeting HER-2/neu-overexpressing breast and ovarian cancer, *Adv. Exp. Med. Biol.*, 465: 171-80 (2000).

Ireton et al., spo0J is required for normal chromosome segregation as well as the initiation of sporulation in *Bacillus subtilis*, *J. Bacteriol.*, 176: 5320 (1994).

Janoff, A., ed., Liposomes, Rational Design. New York: Marcel Dekker (1998).

Jones et al., Replacing the complementarity-determining regions in a human antibody with those from a mouse, *Nature*, 321: 522-525 (1986).

Kaetzel et al., The polymeric immunoglobulin receptor: structure and synthesis, *Biochem. Soc. Trans.*, 25: 475-480 (1997).

Karpovsky et al., Production of target-specific effector cells using hetero-cross-linked aggregates containing anti-target cell and anti-Fc gamma receptor antibodies, *J. Exp. Med.*, 160(6): 1686-701 (1984).

Kemp et al., Amifostine pretreatment for protection against cyclophosphamide induced and cisplatin-induced toxicities: results of a randomized control trial in patients with advanced ovarian cancer, *J. Clin. Oncol.*, 14: 2101-2112 (1996).

Kerem et al., "Identification of the cystic fibrosis gene: genetic analysis," *Science*, 245: 1073 (1989).

Kirmani et al., A comparison of intravenous versus intraperitoneal chemotherapy for the initial treatment of ovarian cancer, *Gynecol. Oncol.*, 54(3): 338-344 (1994).

Kleeff et al., Targeting of suicide gene delivery in pancreatic cancer cells via FGF receptors, *Cancer Gene Ther.*, 9(6): 522-32 (2002).

Knappik et al., Fully synthetic human combinatorial antibody libraries (HuCAL) based on modular consensus frameworks and CDRs randomized with trinucleotides, *J. Mol. Biol.*, 296: 57-86 (2000).

Kostelny et al., Formation of a bispecific antibody by the use of leucine zippers, *J. Immunol.*, 148(5): 1547-53 (1992).

Kumanohoso et al., Enhancement of therapeutic efficacy of bleomycin by incorporation into biodegradable poly-d,l-lactic acid, *Cancer Chemother. Pharmacol.*, 40: 112-116 (1997).

Lasic & Martin, editors, Stealth liposomes. Boca Raton: CRC Press (1995).

Lasic & Papahadjopoulos, editors, Medical Applications of Liposomes. New York: Elsevier (1998).

Levin et al., "Identification of *Bacillus subtilis* genes for septum placement and shape determination," *J. Bacteriol.*, 174: 6717 (1992).

Mekhail & Markman, Paclitaxel in cancer therapy, *Expert Opin. Pharmacother.*, 3: 755-766 (2002).

Norris et al., Phase III comparative study of vinorelbine combined with Doxorubicin versus Doxorubicin alone in disseminated metastatic/recurrent breast cancer, *J. Clin. Oncol.*, 18: 2385-94 (2000).

Okada et al., "Possible function of the cytoplasmic axial filaments in chromosomal segregation and cellular division of *Escherichia coli*," *Sci. Prog.*, 77: 253 (1993-94).

Okada et al., "Cytoplasmic axial filaments in *Escherichia coli* cells: possible function in the mechanism of chromosome segregation and cell division," *J. Bacteriol.*, 176: 917 (1994).

Osbourn et al., Current methods for the generation of human antibodies for the treatment of autoimmune diseases, *Drug Delivery Tech.*, 8: 845-851 (2003).

Pack & Pluckthun, Miniantibodies: use of amphipathic helices to produce functional, flexibly linked dimeric Fv fragments with high avidity in *Escherichia coli*, *Biochemistry*, 31(6): 1579-84 (1992).

Paridaens et al., Paclitaxel versus Doxorubicin as first-line single-agent chemotherapy for metastatic breast cancer, *J. Clin. Oncol.*, 18: 724-33 (2002).

Pikaar et al., "Opsonic activities of surfactant proteins A and D in phagocytosis of gram-negative bacteria by alveolar macrophages," *J. Infect. Dis.*, 172: 481 (1995).

Prasher et al., "Using GFP to see the light," *Trends in Genetics*, 11: 320 (1995).

Puisieux et al., editors, Liposomes, New Systems and New Trends in Their Applications. Paris: Editions de Sant'e (1995)

Raskin & de Boer, "MinDE-dependent pole-to-pole oscillation of division inhibitor MinC in *Escherichia coli*," *J. Bacteriol.*, 181: 6419 (1999).

Reeve, "Use of minicells for bacteriophage-directed polypeptide synthesis," *Methods Enzymol.*, 68: 493 (1979).

Ridgway et al., 'Knobs-into-holes' engineering of antibody CH3 domains for heavy chain heterodimerization, *Protein Eng.*, 9(7): 617-21 (1996).

Riechmann et al., Reshaping human antibodies for therapy, *Nature*, 332: 323-327 (1988).

Riezman, "Three clathrin-dependent budding steps and cell polarity," *Trends in Cell Biology.*, 3: 330 (1993).

Riordan et al., "Identification of the cystic fibrosis gene: cloning and characterization of complementary DNA," *Science*, 245: 1066 (1989).

Rommens et al., "Identification of the cystic fibrosis gene: Chromosome walking and jumping," *Science*, 245: 1059 (1989).

Salomon et al., Epidermal growth factor-related peptides and their receptors in human malignancies, *Crit. Rev. Oncol. Hematol.*, 19: 183-232 (1995).

Sandvig & Deurs, "Endocytosis without clathrin," *Trends in Cell Biology*, 4: 275 (1994).

Sarosy & Reed, Taxol dose intensification and its clinical implications, *J. Natl. Med. Assoc.*, 85(6): 427-31 (1993).

Schiller et al., Amifostine, Cisplatin, and Vinblastine in metastatic non-small cell lung cancer: a report of high response rates and prolonged survival, *J. Clin. Oncol.*, 14: 1913-1921 (1996).

Shangara et al., "Suicide genes: past, present and future perspectives," *Immunology Today*, 21: 48 (2000).

Shapiro et al., A randomized comparison of intra-arterial versus intravenous BCNU, with or without intravenous 5-fluorouracil, for newly diagnosed patients with malignant glioma, *J. Neurosurg.*, 76: 772-781 (1992).

Sharma et al., Novel Taxol formulation: polyvinylpyrrolidone nanoparticle encapsulated Taxol for drug delivery in cancer therapy, *Oncology Res.*, 8(8-9): 281-286 (1996).

Sheets et al., Efficient construction of a large nonimmune phage antibody library: the production of high-affinity human single-chain antibodies to protein antigens, *Proc. Natl. Acad. Sci. USA*, 95: 6157-6162 (1998).

Sipos et al., Optimizing interstitial delivery of BCNU from controlled release polymers for the treatment of brain tumors, *Cancer Chemother. Pharmacol.*, 39: 383-389 (1997).

Slepushkin et al., Sterically stabilized pH-sensitive liposomes. Intracellular delivery of aqueous contents and prolonged circulation in vivo, *J. Biological Chem.*, 272(4): 2382-2388 (1997).

Speert et al., "Functional characterization of macrophage receptors for In-vitro phagocytosis of unopsonized pseudomonas-aeruginosa," *J. Clin. Invest.*, 82: 872 (1988).

Spencer, "Developments in suicide genes for preclinical and clinical applications," *Molecular Therapeutics*, 2: 433 (2000).

Stewart & D'Ari, "Genetic and morphological characterization of an *Escherichia coli* chromosome segregation mutant," *J. Bacteriol.*, 174: 4513 (1992).

Thurnher et al., Carbohydrate receptor-mediated gene transfer to human T leukaemic cells, *Glycobiology*, 4(4): 429-35 (1994).

Todorovska et al., Design and application of diabodies, triabodies and tetrabodies for cancer targeting, *J. Immunol. Methods*, 248: 47-66 (2001).

Tomlinson & Holliger, Methods for generating multivalent and bispecific antibody fragments, *Methods Enzymol.*, 326: 461-479 (2000).

Vaughan et al., Human antibodies with subnanomolar affinities isolated from a large non-immunized phage display library, *Nature Biotechnol.*, 14: 309-314 (1996).

Vaughan et al., Human antibodies by design, *Nature Biotechnol.*, 16: 535-539 (1998).

Verhoeyen et al., Reshaping human antibodies: grafting an antilysozyme activity, *Science*, 239: 1534-1536 (1988).

Wachi et al., "New mre genes mreC and mreD, responsible for formation of the rod shape of *Escherichia coli* cells," *J. Bacteriol.*, 171: 6511 (1989).

White, Liposomal daunorubicin is not recommended in patients with less than advanced HIV related Kaposi's sarcoma, *Aids*, 11: 1412-1413 (1997).

Woodle & Lasic, Sterically stabilized liposomes, *Biochim. Biophys. Acta*, 1113: 171-99 (1992).

Wright & Jong, "Interferon-gamma depresses binding of ligand by c3b and c3bi receptors on cultured human monocytes, an effect reversed by fibronectin," *Experimental Medi.*, 163: 1245 (1986).

Yazawa et al., "Current progress in suicide gene therapy for cancer," *World J. Surg.*, 26: 783 (2002).

Ziady et al., Gene transfer into hepatoma cell lines via the serpin enzyme complex receptor, *Am. J Physiol.*, 273(2 Pt 1): G545-52 (1997).

What is claimed is:

1. A targeted drug delivery method that comprises
   (a) providing a composition comprising (i) at least $10^7$ intact bacterial minicells, wherein said bacterial minicells are derived from *Salmonella typhimurium*, are approximately 400 nm in diameter, and are loaded with a therapeutically effective amount of a chemotherapeutic drug, and (ii) a bispecific antibody having specificity for a cancer cell surface receptor and specificity for said minicells, wherein said bispecific antibody is attached to said minicells, wherein said composition is free of membrane blebs of 200 nm or less in size, wherein said composition contains fewer than about 1 contaminating parent bacterial cell per $10^7$ minicells; and
   (b) contacting said composition with non-phagocytic cancer cells, such that
      (i) said bispecific antibody causes said minicells to bind to said cancer cells,
      (ii) said minicells are engulfed by said cancer cells, and
      (iii) said chemotherapeutic drug is released into the cytoplasm of said cancer cells.

2. The method of claim 1, wherein said bispecific antibody comprises a first arm that carries specificity for a bacterially derived minicell surface structure and a second arm that carries specificity for a non-phagocytic cancer cell surface receptor.

3. The method of claim 2, wherein said first arm and said second arm are monospecific.

4. The method of claim 2, wherein said first arm and said second arm are multivalent.

5. The method of claim 2, wherein said minicell surface structure is an O-polysaccharide component of a lipopolysaccharide on said minicell surface.

6. The method of claim 2, wherein said minicell surface structure is selected from the group consisting of outer membrane proteins, pilli, fimbrae, flagella, and cell-surface exposed carbohydrates.

7. The method of claim 1, wherein said bispecific antibody comprises a humanized antibody.

8. The method of claim 1, wherein said contacting is in vitro.

9. The method of claim 1, wherein said contacting is in vivo.

10. The method of claim 1, wherein said chemotherapeutic drug is doxorubicin and said minicells are loaded with at least 8.5 ng of doxorubicin.

11. The method of claim 10, wherein said minicells are loaded with at least 66 ng of said chemotherapeutic agent.

* * * * *